United States Patent [19]

Kamikado et al.

[11] Patent Number: 4,954,497
[45] Date of Patent: Sep. 4, 1990

[54] ACRYLIC ACID MORPHOLIDES AND FUNGICIDAL COMPOSITIONS

[75] Inventors: Toshiya Kamikado; Yasuyuki Kando, both of Hyogo; Kazuho Matsuura, Kyoto; Junji Yamada, Nara, all of Japan

[73] Assignee: Takeda Chemical Industries, Ltd., Osaka, Japan

[21] Appl. No.: 310,926

[22] Filed: Feb. 16, 1989

[30] Foreign Application Priority Data

Feb. 22, 1988 [JP] Japan .................................. 63-039130
May 24, 1988 [JP] Japan .................................. 63-126358

[51] Int. Cl.$^5$ .................... A01N 43/84; C07D 413/06
[52] U.S. Cl. .................................. 514/235.5; 544/231
[58] Field of Search ..................... 544/131; 514/235.5

[56] References Cited
U.S. PATENT DOCUMENTS 4,753,934 6/1988 Nickl et al. ......................... 544/165

Primary Examiner—Robert W. Ramsuer
Attorney, Agent, or Firm—Wegner & Bretschneider

[57] ABSTRACT

This invention relates to a compound of the formula:

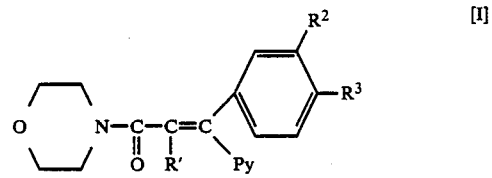

wherein $R^1$ is hydrogen, a halogen or a lower alkyl group; $R^2$ and $R^{33}$ independently are a lower alkoxyl group; and Py is an optionally substituted pyridyl group or a salt thereof.

The compound or a salt thereof exerts excellent fungicidal effects against plant disease and is used as fungicide for agricultural use.

9 Claims, No Drawings

ACRYLIC ACID MORPHOLIDES AND FUNGICIDAL COMPOSITIONS

This invention relates to novel acrylic acid morpholides.

More particularly, this invention relates to an acrylic acid morpholide represented by the formula:

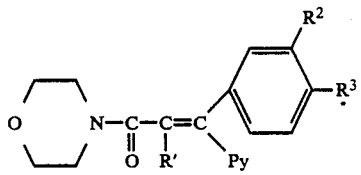
[I]

wherein $R^1$ stands for hydrogen, a halogen atom or a lower alkyl group, $R^2$ and $R^3$ independently stand for a lower alkoxy group, and Py stands for an optionally substituted pyridyl group-or a salt thereof.

It has been known that certain kinds of cinnamic acid derivatives exert a fungicidal activity against pathogenic microorganisms causing various plant diseases. For example, the compounds described in EP-A 120321 have been known to be effective against downy mildew of grape, cucumber, etc. or late blight of tomato, potato, etc.

However, these known compounds do not show practically satisfactory preventing and controlling effects against plant diseases, and discovery of more effective compounds are desired. Especially, downy mildew or late blight, which has been considered as principal cause of diseases of vegetables or fruits, is apt to occur and spread in the rainy season, and, in such wet season, even if conventional drugs including the above-mentioned known compounds are sprayed, the drugs sprayed are washed away by rain. Thus no satisfactory effect has been attained.

The present inventors conducted considerable and extensive research work with a specific view to complying with such demands as finding compounds whose effects are scarcely reduced even by rainfall after their spray, which has culminated in the present invention.

The compound [I] or a salt thereof, based on the characteristic feature of its chemical structure, shows preventive effect, especially showing excellent fungicidal effects even after the rainfall after spraying, against plant diseases, especially downy mildew and late blight which cause serious damage to vegetables or fruits, superior to those of known compounds.

In the above formula, $R^1$ stands for hydrogen, a halogen atom or a lower alkyl group. Examples of the halogen atom shown by $R^1$ include Cl, Br, I and F. The lower alkyl group shown by $R^1$ is preferably a straight-chain or branched $C_{1-4}$ alkyl group, for example, methyl, ethyl, n-propyl, i-propyl, n-butyl or i-butyl. Preferable example of $R^1$ is hydrogen.

$R^2$ and $R^3$ show the same or different lower alkoxy groups. The lower alkoxy group shown by $R^2$ and $R^3$ is preferably a straight-chain or branched $C_{1-4}$ alkoxy group, such as methoxy, ethoxy, n-propoxy, i-propoxy, n-butoxy or i-butoxy. More preferably $R^2$ and $R^3$ independently are a straight-chain or branched $C_{1-3}$ alkoxy group, such as methoxy, ethoxy, propoxy or isopropoxy. The cases where $R^2$ and $R^3$ both stand for methoxy are most preferable.

Py stands for an optionally substituted pyridyl group. As the optionally substituted pyridyl group shown by Py, use is made of a group represented by the formula:

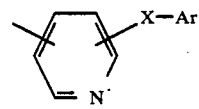

wherein X stands for a chemical bond, —Alk—, —O—(Alk)n—,

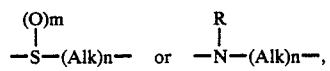

in which m denotes 0,1 or 2, n denotes 0 or 1, R stands for hydrogen or a lower alkyl group, and Ar is an optionally substituted aryl group or an optionally substituted heterocyclic group.

In the above, Alk stands for a lower alkylene group, a lower alkenylene group or a lower alkynylene group. As the lower alkylene group shown by Alk, use is made of a straight-chain or branched $C_{1-4}$ alkylene group, such as —$CH_2$—, —$CH_2CH_2$—, —$CH_2CH_2CH_2$—, $$-CH_2\overset{CH_3}{\underset{|}{CH}}-, \quad -\overset{CH_3}{\underset{|}{CH}}CH_2CH_2-$$

or —$(CH_2)_4$—. As the lower alkenylene group shown by Alk, use is made of a straight-chain or branched $C_{2-4}$ alkenylene group, such as —CH=CH—, —CH=CH—$CH_2$—, $$-\overset{CH_3}{\underset{|}{CH}}-CH=CH-,$$

—CH=CH—CH=CH— or —$CH_2$—CH=CH—$CH_2$—. As the lower alkynylene group shown by Alk, use is made of for example, straight-chain or branched $C_{2-4}$ alkynylene group, such as —C≡C—, —C≡C—$CH_2$—, $$-\overset{CH_3}{\underset{|}{CH}}-C\equiv C-,$$

—$CH_2CH_2$—C≡C—, $$-\overset{CH_3}{\underset{|}{CH}}CH_2-C\equiv C-, \text{ etc.}$$

As the lower alkyl group shown by R, use is made of a straight-chain or branched $C_{1-4}$ alkyl group as mentioned referring to the above $R^1$. Preferable examples of X include a chemical bond, —$CH_2$—, —$CH_2CH_2$—, —O—, —S—, —$OCH_2$—, —$SCH_2$— or

in which R is of the same meaning as defined above. More preferably X is —O—. As the aryl group shown by Ar, use is made of a $C_{6-10}$ aryl group, such as phenyl or naphthyl. The heterocyclic group shown by Ar is a group formed by removing one hydrogen atom bonding to the carbon atom of the heterocyclic group. As the heterocyclic group, use is made of a 5- to 8-membered heterocyclic group containing one to several, preferably 1 to 4, hetero atoms, such as a nitrogen atom which may be oxidised, an oxygen atom or a sulfur atom and one to seven carbon atoms, or a condensed ring with the 5 to 6 membered heterocyclic ring containing one to two heteroatoms selected from the class consisting of nitrogen and sulfur, and 1 to 5 carbon atoms. Specific examples of the heterocyclic group include 2- or 3-pyrrolyl, 3-,4- or 5-pyrazolyl, 2-,4- or 5-imidazolyl, 1,2,3- or 1,2,4-triazolyl, 1H— or 2H—tetrazolyl, 2- or 3-furyl, 2- or 3-thienyl, 2-,4- or 5-oxazolyl, 3-,4- or 5-isoxazolyl, 1,2,3-oxadiazol-4- or 5-yl, 1,2,4-oxadiazol-3- or 5-yl, 1,2,5- or 1,3,4-oxadiazolyl, 2-,4- or 5-thiazolyl, 3-,4- or 5-isothiazolyl, 1,2,3-thiadiazol-4- or 5-yl, 1,2,4-thiadiazol-3- or 5-yl, 1,2,5- or 1,3,4-thiadiazolyl, 2- or 3-pyrrolidinyl, 2-,3- or 4-pyridyl, 2-,3- or 4-pyridyl-N-oxide, 3- or 4-pyridazinyl, 3- or 4-pyridazinyl-N-oxide, 2-, 4- or 5-pyrimidinyl, 2-, 4- or 5-pyrimidinyl-N-oxide, pyrazinyl, 2-,3- or 4-piperidinyl, piperazinyl, indolyl, benzofuranyl, benzothienyl, 2-,3- or 4-pyranyl, 2-,3- or 4-thiopyranyl, benzopyranyl, quinolyl, pyrido[2,3-d]pyrimidyl, 1,5-, 1,6- 1,7-, 1,8-, 2,6- or 2,7-naphthylidinyl, thieno[2,3-d]pyridyl, pyrimidopyridyl, pyrazinoquinolyl and benzopyranyl. The aryl group and heterocyclic group shown by Ar may be substituted with one or the same or different two to five substituents. As these substituents, use is made of a halogen atom (fluorine, chlorine, bromine or iodine), nitro, an optionally halogeno-substituted $C_{6-10}$ aryl group (e.g. phenyl, p-chlorophenyl, p-fluorophenyl or naphthyl), a lower alkyl group (e.g. a straight-chain or branched $C_{1-4}$ alkyl group, such as methyl, ethyl, propyl, isopropyl, butyl, isobutyl or t-butyl), a lower alkoxy group (e.g. a straight-chain or branched $C_{1-4}$ alkoxy group, such as methoxy, ethoxy, propoxy, isopropoxy, butoxy, isobutoxy or t-butoxy), a lower alkylthio group (e.g. a straight-chain or branched $C_{1-4}$ alkylthio group, such as methylthio, ethylthio, propylthio, isobutylthio or t-butylthio), a lower alkylsulfonyl group (e.g. a straight-chain or branched $C_{1-4}$ alkylsulfonyl group, such as methylsulfonyl, ethylsulfonyl, propylsulfonyl, isopropylsulfonyl, butylsulfonyl or isobutylsulfonyl), a lower halogenoalkyl group (e.g. a straight-chain or branched halogeno-$C_{1-4}$ alkyl group, such as chloromethyl, bromomethyl, fluoromethyl, dichloromethyl, difluoromethyl, trifluoromethyl, 1-chloroethyl, 2,2,2-trichloroethyl, 1-chloropropyl, 2,3-dichloropropyl, 2,3-dibromopropyl, 3-iodopropyl, 3,3,3-trichloropropyl or 1-chlorobutyl), a lower halogenoalkoxy group (e.g. a straight-chain or branched halogeno-$C_{1-4}$ alkoxy group, such as chloromethoxy, dichloromethoxy, difluoromethoxy, trifuoromethoxy, chlorodifluoromethoxy, 2-chloroethoxy, 2-bromoethoxy 2,2,2-trifluoroethoxy, bromodifluoromethoxy, 1,1,2,2-tetrafluoroethoxy, 2-chloro-1,1,2-trifluoroethoxy, 3-chloropropoxy, 3-iodopropoxy, 2,2,3,3-tetrafluoropropoxy, 2,3-dichlorobutoxy or 2,3-dichloroisobutoxy), a lower halogenoalkylthio group (e.g. a straight-chain or branched halogeno-$C_{1-4}$ alkylthio group, such as chloromethylthio, difluoromethylthio, trifluoromethylthio, chlorodifluoromethylthio, 2-chloroethylthio, 2,2,2-trifluoroethylthio, bromodifluoromethylthio, 1,1,2,2-tetrafluoroethylthio, 2-chloro-1,1,2-trifluoroethylthio, 3-chloropropylthio, 2,2,3,3-tetrafluoropropylthio, 4-chlorobutylthio, 4-bromobutylthio), a lower halogenoalkylsulfonyl group (e.g. a straight-chain or branched halogeno-$C_{1-4}$ alkylsulfonyl group, such as chloromethylsulfonyl, difluoromethylsulfonyl, 2-chloroethylsulfonyl or 4-bromobutylsulfonyl, 1,1,2,2-tetrafluoroethylsulfonyl). Preferable examples of Ar include a $C_{6-10}$ aryl group (e.g. phenyl or naphthyl), and the aryl group may be substituted with 1, 2 or 3 groups, such as a halogen atom (e.g. chlorine, bromine or fluorine), $C_{1-4}$ alkyl (e.g. methyl or ethyl), halogeno-$C_{1-4}$ alkyl (e.g. trifluoromethyl), $C_{1-4}$ alkoxy (e.g. methoxy or ethoxy) or phenyl. And, preferable examples of optionally substituted pyridyl group shown by Py include groups represented by the formula:

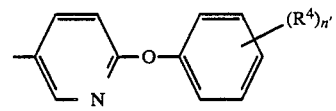

or

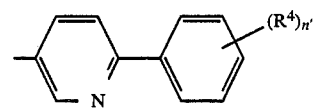

or

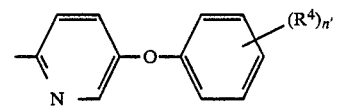

or

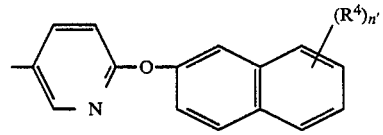

wherein $R^4$ stands for a halogen atom, a lower alkyl group, a lower halogenoalkyl group, a phenyl group or a lower alkoxy group, and $n^1$ denotes 1, 2 or 3. As the halogen atom, lower alkyl group and lower alkoxy group shown by $R^4$, use is made of those described regarding the above-mentioned substituents at Ar. Preferable Examples of Py include 2-(4-chlorophenoxy)-5-pyridyl, 2-(3-chlorophenoxy)-5-pyridyl, 2-(4-bromophenoxy)-5-pyridyl, 2-(4-fluorophenoxy)-5-pyridyl, 2-(2-chloro-4-fluorophenoxy)-5-pyridyl, 2-(2,4-dichlorophenoxy)-5-pyridyl, 2-(3,4-dichlorophenoxy)-5-pyridyl, 2-(4-methylphenoxy)-5-pyridyl, 2-(4-trifluoromethylphenoxy)-5-pyridyl, 2-(4-phenylphenoxy)-5-pyridyl, 2-(4-methoxyphenoxy)-5-pyridyl, 2-(4-chlorophenyl)-5-pyridyl, 5-(4-chlorophenoxy)-2-pyridyl, 2-($\beta$-naphthoxy)-5-pyridyl, 2-(2-bromo-5-fluorophenoxy)-5-pyridyl, 2-(4-bromo-2,6-difluorophenoxy)-5-pyridyl, 2-(4-bromo-2-methylphenoxy)-5-pyridyl and 2-(3-methylphenoxy)-5-pyridyl.

Preferably Py is a group of the formula:

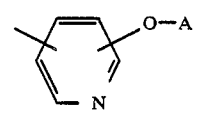

wherein A is a $C_{6-10}$ aryl group which may be substituted by a halogen atom, a $C_{1-3}$ alkyl group or/and a $C_{1-3}$ alkoxy group, the number of the substituents being 1 to 3.

More preferably, Py is a group of the formula:

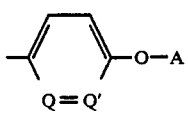

wherein either of Q and Q' is N and the other is CH; and the other symbols are as defined above.

Preferable examples of the compound [I] or a salt thereof include compounds represented by the formula:

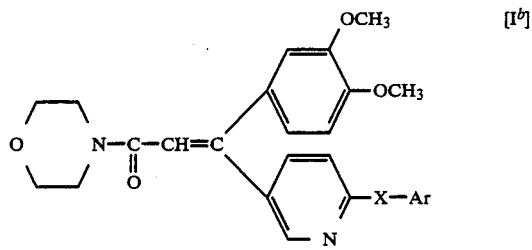

wherein the symbols are of the same meaning as defined above. Especially preferable examples of the compound [I] or a salt thereof include those represented by the formula:

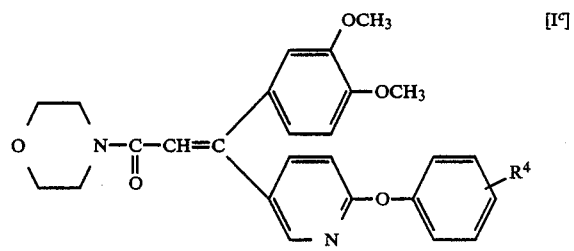

wherein the symbols are of the same meaning as defined above.

Additionally, the compound [I] or a salt thereof includes E- and Z-isomers in connection with the steric configuration of the group —CH=C<, singly and in admixture of them.

The compound [I] can form an acid addition salt thereof. As the salt of compound [I], an agriculturally nontoxic acid addition salt is used. Examples of the acid include an inorganic acid, such as sulfuric acid, hydrochloric acid or perchloric acid and an organic acid, such as methanesulfonic acid, trifluoro methanesulfonic acid, p-toluenesulfonic acid or benzene sulfonic acid. The later-mentioned compounds [III], [V], [VII], [VIII] and [X] may form an addition salt with the acid as mentioned above.

The compound [I] or a salt thereof possesses excellent fungicidal activities against various phytopathogenic microorganisms.

The compound [I] or a salt thereof exhibits remarkable controlling effects on, among various plant diseases caused by pathogenic microorganisms, especially downy mildew on vegetables such as cucumber, potato, Chinese cabbage, onion or beans, or late blight on tomato, potato, green pepper or pumpkin. Further, the compound [I] or a salt thereof maintains the fungicidal effect for a considerably long period of time after applying to plants (long-lasting effect), and suffers less in reduction of the efficacy due to little washing off by rain after application by spraying (rain-resistance effect). Thus, the compound [I] or a salt thereof exerts sufficient effects even in the rainy season when downy mildew or late blight occurs frequently.

The compound [I] or a salt thereof is of low toxicity to warm-blooded animals and less effective in bringing about undesirable impact on the environment. Thus, the compound [I] or salt thereof is conspicuously excellent as fungicidal agent for the agricultural use.

When the compound [I] or a salt thereof is used as fungicidal agents, two or more kinds of these compounds [I] may be used in combination, or one kind may be used alone.

The compound [I] or a salt thereof may be used as it is, or may be dissolved or dispersed in a suitable liquid carrier (for example, a solvent) or admixed with or adsorbed on an appropriate solid carrier (for example, a diluent or an extender), followed by, if necessary, further adding an emulsifying agent, suspending agent, spreader, penetrant, wetting agent, thickening agent, stabilizer, etc. thereto to use as emulsifiable concentrates, wettable powders, oil preparation, dusts, granules, and other suitable preparation forms. These preparations can be made by conventional processes.

The weight ratio of the compound [I] or a salt thereof relative to the total fungicidal composition may suitably be in the range of about 1 to 80 weight % for emulsifiable concentrates and wettable powders, about 0.1 to 10 weight % for oil preparation, dusts, etc., and 5 to 50 weight % for granules. These ratios may suitably be changed upon conditions when used or circumstances of occurrence of disease injuries. The emulsifiable concentrates and wettable powders, in bringing into practical use, may be suitably diluted with water, etc. (for example, up to 100 to 5,000 times) to be sprayed.

As liquid carriers (solvent) to be employed for the fungicidal agent according to the present invention, use is made of water, alcohols (e.g. methyl alcohol, ethyl alcohol, isopropyl alcohol or ethylene glycol), ketones (e.g. acetone or methyl ethyl ketone), ethers (e.g. dioxane, tetrahydrofuran or cellosolve), aliphatic hydrocarbons (e.g. gasoline, kerosene, fuel oil, machine oil), aromatic hydrocarbons (e.g. benzene, toluene, xylene, solvent naphtha or methylnaphthalene), or halogenated hydrocarbons (e.g., 1,2-dichloroethane, chloroform or carbon tetrachloride), acid amides (e.g. dimethylformamide), esters (e.g. ethyl acetate, butyl acetate, mono- or di- or tri-glycerine esters of fatty acids containing 3 to 20 carbon atoms), nitriles (e.g. acetonitrile), and the like. These solvents may be used solely or as a mixture of two or more kinds in an appropriate mixing ratio.

Operable as the solid carriers (diluent, extender) may be, for example, a powder of plant origin (e.g., soybean powder, tobacco powder, wheat flour, wood powder, etc.), powder of mineral origin (e.g., kaolin, bentonite, clays such as acid clay, talcs such as talc powder, pagotite powder, etc., silicas such as diatomaceous earth, mica powder, etc., and alumina, sulfur powder, calcium phosphate, activated carbon, etc. which may be used solely or as a mixture of not less than two kinds in an appropriate ratio.

Examples of surfactants employed as the emulsifying agent, suspending agent, spreader, penetrant, dispersing agent and the like include soaps, polyoxyalkyl aryl esters (e.g. Nonal ®, manufactured by Takemoto Yushi K. K.), alkyl sulfates (e.g. Emal 10 ®, Emal 40 ®, manufactured by Kao Atlas K. K.), alkyl sufonates (e.g. Neogen T ®, Neogen T ®, manufactured by Dai-ichi Kogyo Seiyaku K. K.: Neoplex ®, manufactured by Kao Atlas K. K.), polyethylene glycol ethers (e.g. Nonipol 85 ®, Nonipol 100 ®, Nonipol 160 ®, manufactured by San-yo Kasei K. K.), polyhydric alcohol esters (e.g. Tween 20 ®. Tween 80 ®, manufactured by Kao Atlas K. K.), and the like.

The fungicidal agents according to the present invention can be sprayed on the plants at any stage ranging from seedlings to preharvesting stage, and on different stage of seeds. The fungicidal agents according to the present invention can be used for preventing the occurrence of plant diseases by spraying beforehand, and also can be used immediately after the outbreak of diseases.

In case of using the compound [I] or a salt thereof as fungicidal agent for agricultural use, the amount varies depending upon the growing stage of the plant to be treated, its growth condition, species of microorganisms, degree of infestation, application time or method for the fungicidal agent and other conditions, and may generally be adjusted in such a way that the compound [I] or a salt thereof may be at an application rate within the range of 3 to 300 g per 10 are. The application concentration may be in the range of 10 to 1000 ppm of the active component, while the application may be by means of direct spraying, and direct dusting on plants and soil treatment or dust coating of seeds. The application method, if it secures the safe and effective application on plants does not impose any restriction on the present invention. In addition, suitably mixed, as occasion demands, may be different kinds of fungicides (e.g. organochlorine fungicides, organophosphorus fungicides, benzimidazole fungicides, copper fungicides, organic sulfur fungicides, phenol fungicides, triazole fungicides, pyrimidine fungicides, acid amide fungicides, sulfenamide fungicides, amino acid fungicides, antibiotics, etc.), insecticides (e.g. natural insecticides, carbamate insecticides, organic phosphorus insecticides, synthetic pyrethroid, etc.), miticides, nematocides, herbicides, plant growth regulators, stabilizers, synergists, attractant, repellents, perfumes, plant nutrients, fertilizers, various amino acids, low-molecular or high-molecular weight phosphoric acid salts, etc., while metal salts may be added for the purpose of strengthening the effectiveness.

The compound [I] or a salt thereof is produced by reacting a compound represented by the formula:

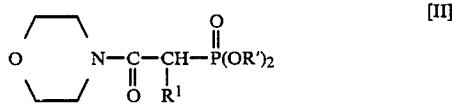

[II]

wherein R' stands for an optionally substituted hydrocarbon group, and $R^1$ is of the same meaning as defined above with a compound represented by the formula:

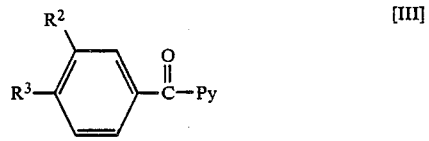

[III]

wherein the symbols are of the same meaning as defined above, or a salt thereof.

R' stands for an optionally substituted hydrocarbon group. Examples of the hydrocarbon group shown by R' include a straight-chain or branched $C_{1-6}$ alkyl group, such as methyl, ethyl, n-propyl, i-propyl, n-butyl, i-butyl, n-pentyl or n-hexyl, a straight-chain or branched $C_{3-6}$ alkenyl group, such as allyl, isopropenyl or 3-butenyl, a straight-chain or branched $C_{3-6}$ alkynyl group, such as 2-butynyl or 2-propynyl, a $C_{3-8}$ cycloalkyl group, such as cyclopropyl, cyclobutyl, cyclopentyl or cyclohexyl, a $C_{3-8}$ cycloalkenyl group, such as 1-cyclopropenyl, 1-cyclobutenyl, 2-cyclopentenyl or 1,4-cyclohexadienyl, a $C_{6-10}$ aryl group, such as phenyl, α-naphthyl or β-naphthyl, a $C_{7-10}$ aralkyl group, such as benzyl or phenethyl. The hydrocarbon group shown by R' may be substituted by 1 to 4 groups exemplified by halogen atoms, such as chlorine or bromine, a straight-chain or branched $C_{1-4}$ alkoxy group, such as methoxy, ethoxy, n-propoxy or i-propoxy. Preferable examples of R' include a straight-chain or branched $C_{1-4}$ alkyl group, such as methyl, ethyl, n-propyl, i-propyl or n-butyl.

In this reaction, the compound [II] may be used usually in an amount ranging from about equimole to 3 moles, preferably about 1 to 1.2 moles per 1 mol of the compound [III]. The reaction temperature is in the range of about 0° C. to 120° C., preferably from about 10° C. to 100° C. This reaction is usually carried out in a solvent which does not hamper the reaction. The solvent is exemplified by aromatic hydrocarbons such as benzene, toluene, xylene, chlorobenzene, etc., aliphatic hydrocarbons such as hexane, heptane or octane, halogenated hydrocarbons such as dichloromethane, chloroform or 1,2-dichloroethane, ethers such as diethyl ether, diisopropyl ether, tetrahydrofuran, dioxane or 1,2-dimethoxyethane, esters such as methyl acetate or ethyl acetate, nitriles such as acetonitrile, alcohols such as methanol, ethanol, isopropanol, butanol or t-butanol, nitrobenzene, dimethyl sulfoxide, amides such as dimethylformamide, dimethylacetamide, N-methylpyrrolidone; and tert-amine such as pyridine, picoline, 2-methyl-5-ethylpyridine, collidine or triethylamine. These solvents may be used, solely or, upon necessity, as a mixture of two or more of them at suitable ratios.

This reaction proceeds advantageously in the presence of a base. Examples of the base include an organic amine such as triethylamine, N-methylpiperidine, 1,8-diazabicyclo[5,4,0]-7-undecene (hereinafter abbreviated as DBU) or 4-dimethylaminopyridine; alkali metal carbonate such as sodium carbonate or potassium carbonate; alkali metal hydride such as sodium hydride, or lithium hydride; alkali metal hydroxide such as sodium hydroxide or potassium hydroxide; alkali metal alkoxide such as potassium-t-butoxide, sodium methoxide or sodium ethoxide. When these bases are insoluble in a solvent, the reaction can be accelerated by adding to the reaction system a phase-transfer catalyst such as trioctylmethyl ammonium chloride, triethyl benzyl ammonium chloride. The reaction time, which varies with the kinds of starting materials and solvent, and reaction temperature, etc., and ranges usually from about two minutes to 30 hours.

Alternatively, the compound [I] or a salt thereof is produced by reacting a carboxylic acid represented by the formula:

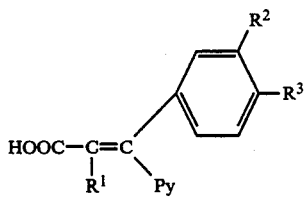

wherein the symbols are of the same meaning as defined above, or a salt thereof or a reactive derivative thereof with morpholine.

The salts of the compound [IV] include those at the carboxyl group with a base such as triethylamine, tripropylamine, morpholine, N-methyl morpholine, N,N-dimethyl aniline, pyridine, picoline or DBU, and those at the pyridyl group with an acid as mentioned for the salt of compound [I]. As the reactive derivative, the reactive derivative at the carboxyl group thereof is used. The reactive derivative includes esters such as methyl ester, ethyl ester, phenyl ester or p-nitrophenyl ester; acid halides such as acid chloride or acid bromide; acid anhydrides with benzoic acid, phosphoric acid, and active azolides such as imidazolide, pyrazolide or triazolide. These can be respectively synthesized by methods conventionally used for carboxylic acids in general.

Relative to the amount of the compound [IV], a salt thereof or a reactive derivative thereof at its carboxyl group, morpholine is preferably used in an amount ranging from equimole to 3 times as much mol. The reaction is carried out in the absence of solvent, or in a solvent which does not hamper the reaction. As the solvent, use is made of aromatic hydrocarbons such as benzene, toluene, xylene, tetralin, etc., aliphatic hydrocarbons such as hexane, heptane, decane, decalin, etc., halogenated hydrocarbons such as dichloromethane, chloroform, carbon tetrachloride, 1,2-dichloroethane, chlorobenzene, dichlorobenzene, etc., esters such as diethyl ether, diisopropyl ether, tetrahydrofuran, dioxane, 1,2-dimethoxyethane, diphenyl ether, etc., esters such as ethyl acetate, methyl acetate, etc., ketones such as acetone, ethyl methyl ketone, isopropyl methyl ketone, etc., amides such as dimethylformamide, dimethylacetamide, etc., acetonitrile, t-butanol, nitrobenzene, dimethylsulfoxide, water, etc. These solvents may be used solely or as a mixture of two or more of them at suitable ratios, for example, ranging from 1:1 to 1:10. In case of using a mixed solvent, and when the mixed solvent is not of homogeneous phase, the reaction may be allowed to proceed in the presence of a phase-transfer catalyst.

This reaction may be conducted in the presence of an acid acceptor. As the acid acceptor, use is made of, for example, inorganic and organic bases such as alkali metal hydrogen carbonate (e.g. sodium hydrogen carbonate, potassium hydrogen carbonate, etc.), alkali metal carbonate (e.g. sodium carbonate, potassium carbonate, etc.), alkali metal hydroxide (e.g. potassium hydroxide, sodium hydroxide, etc.), trimethylamine, triethylamine, tributylamine, N-methylmorpholine, N-methylpiperidine, N,N-dimethylaniline, pyridine, picoline, lutidine, or the like. The above-mentioned organic bases are used in an amount of one molecular weight or more relative to the compound [IV] and may be used also as solvent.

The reaction between the compound [IV] and morpholine may be carried out in the presence of a dehydrating agent. As the dehydrating agent, use is made of, for example, carbodiimides such as dicyclohexylcarbodiimide, diisopropylcarbodiimide, azodicarboxylic acid esters such as methyl azodicarboxylate, ethyl azodicarboxylate, etc., a combination of carbon tetrachloride and triphenylphosphine, etc. These are used usually in an amount of about 1 to 1.5 equivalent relative to the compound [IV]. The reaction temperature, which varies with the kinds of the compound [IV], acid acceptors and dehydrating agents then employed, ranges usually from about −20° C. to 250° C. The reaction time, which varies with the kinds of the compound [IV] or salts thereof or reactive derivatives thereof at the carboxyl group, solvents, acid acceptors and dehydrating agents, ranges usually from about 2 minutes to 20 hours, while it can also be appropriately set relative to the reaction temperatures then employed.

The compound [I] can be produced by subjecting a compound of the formula:

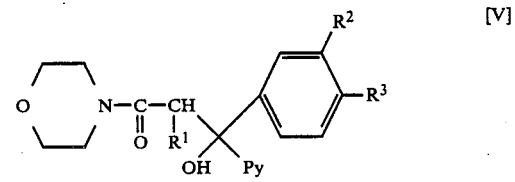

wherein the symbols are as defined above, or a salt thereof to dehydration reaction.

This reaction is usually conducted in the presence of the catalyst or dehydrating agent. Examples of the catalyst include an acid such as an organic acid exemplified by formic acid, acetic acid, propionic acid, benzoic acid, methanesulfonic acid, benzenesulfonic acid or p-toluenesulfonic acid, an inorganic acid exemplified by hydrochloric acid, phosphoric acid, sulfuric acid or nitric acid, a base such as alkali metal hydoxides exemplified by sodium hydroxide or potassium hydroxide, alkoxide exemplified by potassium t-butoxide, sodium methoxide or sodium ethoxide, sodium hydride, DBU or potassium bisulfate. Examples of the dehydrating agent include acid anhydrides exemplified by acetic anhydride or propionic anhydride, acid halides exemplified by acetyl chloride, benzoyl chloride or ethyl chlorocarbonate, phosphor compounds exemplified by phosphorus trichloride, phosphorus pentachloride, phosphorus oxychloride, phosphorus pentoxide, polyphosphoric acid or thionyl chloride.

The catalyst or the dehydrating agent is used in an amount of about 0.1 to 10 moles per 1 mole of the compound [V]. The catalyst may be used as a solvent. The reaction temperature is usually about 0° C. to 200° C. The reaction time is usually about 10 minutes to 30 hours.

The reaction is usually conducted in the presence of the solvent, but may be conducted in the absence of the solvent depending on the condition.

Examples of the solvent include aromatic hydrocarbons such as benzene, toluene, xylene, or tetralin; aliphatic hydrocarbons such as hexane, heptane or decalin; halogenated hydrocarbons such as dichloroethane, chloroform, carbon tetrachloride, 1,2-dichloroethane, chlorobenzene or dichlorobenzene; ethers such as diethyl ether, diisopropyl ether, tetrahydrofuran, dioxane, 1,2-dimethoxyethane or diphenyl ether; esters such as ethyl acetate or methyl acetate; ketones such as acetone, ethyl methyl ketone or isopropyl methyl ketone; amides such as dimethylformamide or dimethylacetamide; alcohols such as methanol, ethanol, isopropanol, n-butanol or t-butanol; acetonitorile, nitrobenzene, dimethylsulfoxide and water.

The solvent may be used singly or as a mixture in a ration of 1:1 to 1:10.

In the case that the mixed solvent is of heterogeneous phase, a phase-transfer catalyst may be added in the solvent.

Further, the compound [I] wherein Py stands for a group of the formula

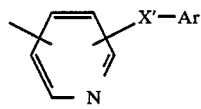

that is the compound of the formula:

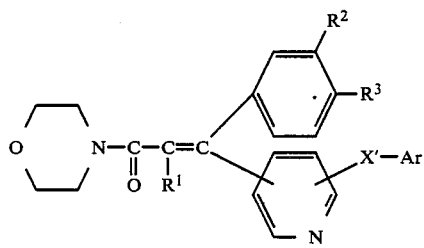 [I$^a$]

wherein X' stands for —O—(Alk)n—, —S—(Alk)n— or

in which Alk stands for a lower alkylene, alkenylene or alkynylene, n denotes 0 or 1 and R stands for hydrogen or a lower alkyl group, and the other symbols are as defined above, or a salt thereof is produced by reacting a compound represented by the formula:

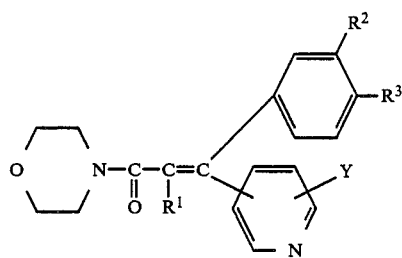 [VI]

wherein Y stands for a halogen atom or a lower alkylsulfonyl group, and other symbols are of the same meaning as defined above with a compound represented by the formula:

 HX'—Ar [VII]

wherein the symbols are of the same meaning as defined above.

Ar stands for an optionally substituted aryl group or an optionally substituted heterocyclic group or a salt thereof.

Examples of the halogen atom shown by Y, include chlorine, bromine, iodine and fluorine. As the lower alkylsulfonyl group shown by Y, use is made of a straight-chain or branched $C_{1-4}$ alkylsulfonyl group such as methylsulfonyl, ethylsulfonyl, n-propylsulfonyl, i-propylsulfonyl, n-butylsulfonyl or i-butylsulfonyl.

In these formulae, as the groups shown by Alk, n and R, use is made of those described regarding the above-mentioned X, respectively. Preferable examples of X' include —O—, —S—, —O—CH$_2$—, —S—CH$_2$— and

wherein R is of the same meaning as defined above.

Examples of the salts of the compound [VII] include salts of an organic tertiary amine such as triethylamine, N-methylmorpholine, N,N-dimethylaniline, pyridine, 4-dimethylaminopyridine or DBU, and salts of a metal such as sodium, potassium, calcium, lithium or copper.

In this reaction, the amount of the compound [VII] or a salt thereof usually ranges from about equimole to 3 moles preferably from about 1 to 1.3 moles relative to 1 mole of the compound [VI]. This reaction is usually carried out in a solvent. Examples of the solvent include hydrocarbons such as benzene, toluene, xylene, hexane, ligroin, etc., ethers such as diethyl ether, diisopropyl ether, tetrahydrofuran, dioxane, 1,2-dimethoxyethane, etc., halogenated hydrocarbons such as chloroform, carbon tetrachloride, methylene chloride, 1,2-dichloroethane, etc., amides such as dimethylformamide, dimethylacetamide, N-methylpyrrolidone, etc., ketones such as acetone, methyl ethyl ketone, etc., esters such as methyl acetate, ethyl acetate, etc., alcohols such as methanol, ethanol, isopropanol, butanol, t-butanol, etc., dimethyl sulfoxide, sulfolane, acetonitrile, water, etc. These solvents can be used solely or, upon necessity, as a mixture of two or more kinds of them in an appropriate ratio. The reaction may be carried out in the presence of an acid acceptor. As the acid acceptor, use is made of inorganic or organic bases, such as alkali metal hydrogen carbonate (e.g. sodium hydrogen carbonate, potassium hydrogen carbonate, etc.), alkali metal carbonate (e.g. sodium carbonate, potassium carbonate, etc.), alkali metal hydroxide (e.g. potassium hydroxide, sodium hydroxide, etc.), sodium hydride, potassium t-butoxide, trimethylamine, triethylamine, tributylamine, N-methylmorpholine, N-methylpiperidine, N,N-dimethylaniline, pyridine, picoline, lutidine, 4-dimethylaminopyridine, DBU, etc. The above-mentioned organic bases can be used as making themselves to serve as solvents. The bases or the salts of the compound [VII] to be employed for carrying out this reaction are sometimes hardly soluble in solvents, and in such cases or when the solvents which are not mixed with one another are employed, a phase-transfer catalyst can be employed for accelerating the reaction. This reaction can be accelerated by the addition of, as the catalyst, about 1 to 10 mol. % of copper halogenide (e.g. cuprous chloride, cupric chloride, cuprous bromide, cupric bromide, cuprous iodide, cupric iodide, etc.). The reaction temperature is within the range of from about 0° C. to 200° C., preferably 20° C. to 150° C. The reaction time varies with the starting materials, solvents, temperatures and acid acceptors, and it ranges usually from 5 minutes to 30 hours, preferably from 20 minutes to 15 hours.

The compound [I] or a salt thereof can also be produced by the following method.

Namely, the compound [I] or a salt thereof can be produced by (i) reacting a compound represented by the formula:

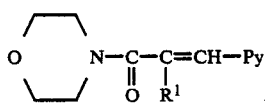
[VIII]

wherein the symbols are of the same meaning as defined above or a salt thereof with a compound represented by the formula:

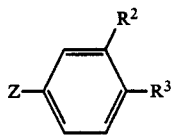
[IX]

wherein Z stands for a halogen atom, and $R^2$ and $R^3$ are of the same meaning as defined above, preferably in the presence of a catalyst such as a palladium catalyst, or (ii) reacting a compound represented by the formula:

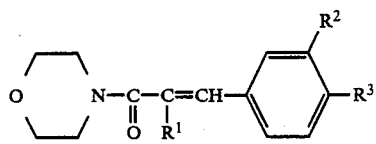
[X]

wherein the symbols are of the same means as defined above with a compound represented by the formula: Z—Py [XI] or a salt thereof wherein the symbols are of the same meaning as defined above, preferably in the presence of a catalyst such as a palladium catalyst.

The above-mentioned reactions (i) and (ii) are both in the category of the reaction called Heck's reaction, and the reaction conditions are practically the same.

As the palladium catalyst to be used for these reactions are exemplified palladium acetate, palladium chloride, tri-arylphosphine-palladium complex, palladium carbon, etc. The reaction is carried out, in most cases, in a solvent, for example, amines such as triethylamine, tripropylamine, etc., alcohols such as methanol, ethanol, butanol, etc., amides such as dimethylformamide, dimethylacetamide, N-methylpyrrolidone, hexamethylphosphoramide, etc., nitriles such as acetonitrile, etc., while the reaction proceeds even in the absence of solvent. The ratios of the compound [VIII] and [IX], and [X] and [XI] are in a range of about 1:20 to 20:1. The reaction temperature ranges from about 10° C. to 200° C., preferably from about 50° C. to 160° C. The amount of the catalyst to be employed ranges usually from 0.1 to 10 mole %. The reaction time, which varies with the kinds of starting materials, palladium catalysts and solvents and reaction temperatures, goes ordinarily to completion within 5 minutes to 30 hours.

The compound [I] or a salt thereof produced thus can be isolated and purified by per se known means, for example, filtration, concentration, concentration under reduced pressure, solvent extraction, phase transfer, pH change, crystallization, recrystallization, distillation, sublimation, salting out, chromatography, etc.

In the methods of producing the compound [I] or a salt thereof described as above, E-isomer and Z-isomer are both produced in the reaction mixture, in most cases. Practically, these isomers are, in most cases, purified and isolated as the mixture, while it may sometimes be possible to isolate each isomer in a pure state in the process of crystallization or chromatography.

Each isomer can be converted to the other isomer by rearrangement by the aid of acid, alkali, heat, light or the like. Of these isomers, that which has substantial biological activity is the E-isomer. However, under the conditions employed in normal biological tests, and in practical use, the isomers are exposed to artificial or natural light to convert the Z-isomer to E-isomer, thus performing satisfactory effects.

The starting compounds [III], [IV], [V] and [VI] or salts thereof are all novel which have never been disclosed in any references, and these compounds can be produced by the following methods or those analogous thereto.

As the salts of compounds [XIII], [XIV], [Va], the same salts as in the compound [I] are used.

The methods of producing the compound [III] and [III'] which is a moiety of [III] or salts thereof are shown by the following reaction scheme.

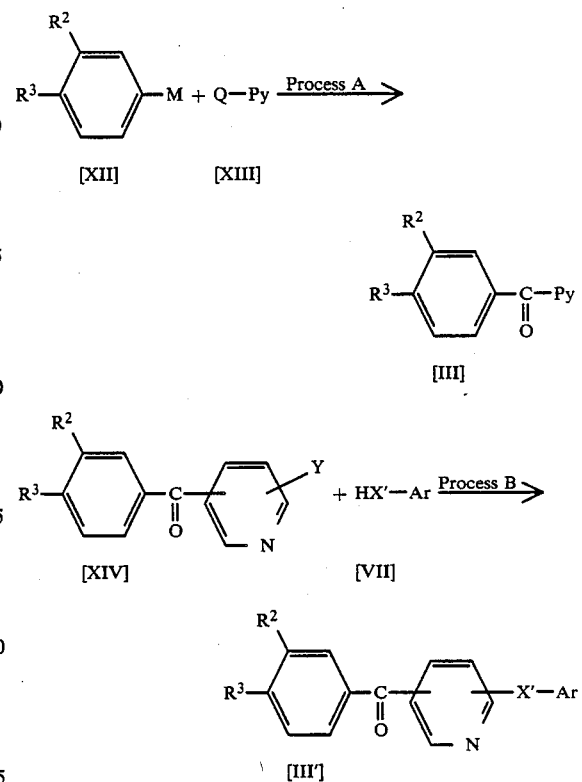

wherein M stands for MgBr, MgCl, MgI or Li, Q stands for chlorocarbonyl, bromocarbonyl or cyano group, and other symbols are of the same meaning as defined above.

Process A

This is a process of obtaining the compound [III] or a salt thereof by reacting the compound [XII] with the compound [XIII] or a salt thereof.

The compound [XII] is, usually in advance, synthesized from the corresponding halogenide and magnesium, lithium or alkyl lithium (e.g. n-butyl lithium) in accordance with a known method, which can be reacted, without isolation, with the compound [XIII] or a salt thereof. And, the compound [XIII] or a salt thereof can be synthesized by the method disclosed, among others, in "Chemical Abstracts" 66, 85678n (1967), or methods analogous thereto.

This reaction may be carried out in a solvent, for example, hydrocarbons such as benzene, toluene, xylene, hexane, etc., or ethers such as diethyl ether, diisopropyl ether, tetrahydrofuran, dioxane, 1,2-dimethoxyethane, etc. The molar ratio of the starting compound [XII] and [XIII] or a salt thereof is usually in the range of 1:3 to 3:1, while a large excess amount of either of the two may be used, as the case may be. The reaction time ranges usually from several minutes to 20 hours, while it is suitably determined taking the kinds of starting compounds and reaction temperatures into consideration.

Incidentally, when Q stands for a cyano group, it is desirable to add an aqueous solution of a mineral acid (e.g. hydrochloric acid, sulfuric acid, etc.) to the reaction mixture so as to promote the hydrolysis of the ketimine, which is produced as an intermediate in the course of the reaction, into ketone.

Process B

This is a process of obtaining the compound [III'] or a salt thereof by reacting the compound [XIV] or a salt thereof with the compound [VII] or a salt thereof.

This process can be conducted in a manner similar to that in the above-mentioned reaction between the compounds VI] and [VII]. And, the starting compound [XIV] can be synthesized by the method of the above-mentioned Process A, and most of the compounds [VII] are commercially available and, besides, can be synthesized by the method disclosed in, for example, "Organic Functional Group Preparations", Vol. 1, p.77 to 98, 318 to 362, 479 to 492 (1968), etc. or methods analogous thereto.

The compound [III] or a salt thereof obtained thus can be used as the starting material in the method of this invention, after isolating and purifying by per se known means as mentioned above or as a reaction mixture.

The starting compound [IV] or its ester can be produced by, for example, the following process. Namely, a compound represented by the formula:

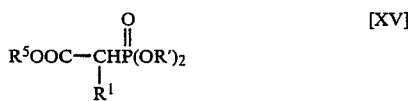

[XV]

wherein $R^5$ stands for a lower alkyl group or phenyl group, and the other symbols are as defined above is reacted with a compound [III] or a salt thereof to give an ester of compound [IV] represented by the general formula:

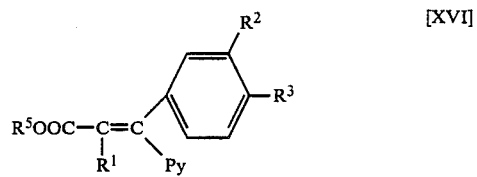

[XVI]

wherein the symbols are as defined above, which is subjected to hydrolysis to obtain the compound [IV].

The reaction between the compounds [XV] and [III] or a salt thereof can be conducted in a manner similar to that of the above reaction between the compounds [II] and [III], or a salt thereof. The hydrolysis of the compound [XVI] can be conducted by any process usually employed for a carboxylic acid ester, for example hydrolysis with alkali metal hydroxide or a mineral acid is often employed Incidentally, the starting compound [XV] is commercially available and can be synthesized by, for example, the methods disclosed in U.S. Pat. No. 3,066,140; "Journal of Organic chemistry" 30, 2208 (1965), etc. or methods analogous thereto.

The compound [IV] obtained thus can be used as the starting material in the method of this invention, after isolating and purifing by the above-mentioned per se known means, or as the reaction mixture itself.

The starting compound (V) or a salt thereof is produced by the following reaction scheme.

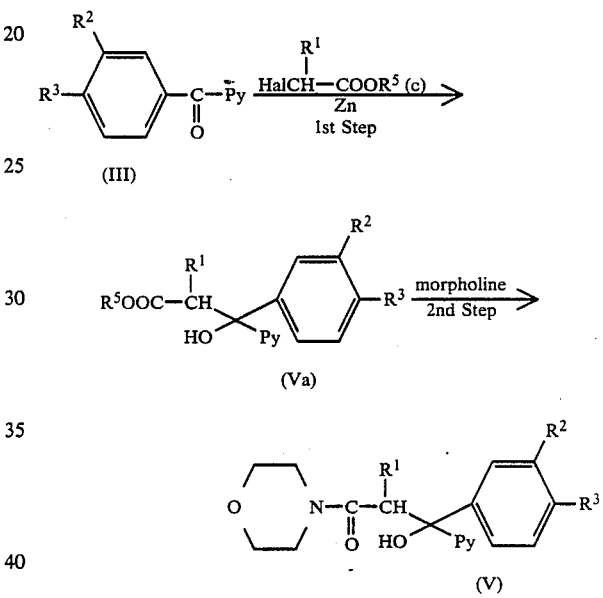

wherein Hal is halogen atom such as chlorine, bromine or iodine and the other symbols are as defined above.

The 1st step of reaction process.

The compound (Va) is produced by reacting the compound (III) or a salt thereof with the compound (c) in the presence of zinc.

The compound (c) is used in an amount of about 1 to 10 moles per 1 mole of the compound (III) or a salt thereof. Zinc is used in an amount of about 1 to 10 moles per 1 mole of the compound (III) or a salt thereof. The reaction is conducted in a solvent which does not hamper the reaction.

Examples of the solvent include aromatic hydrocarbons such as benzene, toluene or xylene; aliphatic hydrocarbons such as hexane or heptane; halogenated hydrocarbons such as dichloromethane, chloroform, carbon tetrachloride, 1,2-dichloroethane or chlorobenzene; and ethers such as diethyl ether, diisopropyl ether, tetrahydrofuran, dioxane, 1,2-dimethoxyethane or diphenyl ether.

The reaction temperature is about 0° C. to 200° C. The reaction time is about 10 minutes to 20 hours.

To accelerate the reaction, ultrasonic irradiation may be conducted and halogenosilane compound, such as chlorotrimethylsilane or dichlorodimethylsilane may be added to the reaction mixture.

The compound obtained can be used in the 2nd step of the reaction process after isolating and purifing by the above-mentioned per se known means, or as the reaction mixture itself.

The 2nd step of reaction process

The compound (V) or a salt thereof is produced by reacting the compound (Va) or a salt thereof with morpholine.

Morpholine is used in an amount of about 1 to 50 moles per 1 mole of the compound (Va) or a salt thereof.

This reaction is conducted in a solvent which does not hamper the reaction.

Examples of the solvent include aromatic hydrocarbons such as benzene, toluene or xylene; aliphatic hydrocarbons such as hexane or heptane; halogenated hydrocarbons such as dichloromethane, chloroform, carbon tetrachloride, 1,2-dichloroethane or chlorobenzene; ethers such as diethyl ether, diisopropyl ether, tetrahydrofuran, dioxane, 1,2-dimethoxyethane or diphenyl ether; ketones such as acetone, ethyl methyl ketone or isopropyl methyl ketone; and dimethylsulfoxide.

The reaction temperature is about 20° C. to 200° C. The reaction time is about 30 minutes to 20 hours. In order to accelerate the reaction, catalyst such as Lewis acid exemplified by boron trifluoride, boron trifluoride diethyl ether complex, aluminium trichloride, zinc chloride, stannic chloride or titanium chloride may be added to the reaction mixture.

Further, the starting compound [VI] can be produced by reacting the compound [II] with the compound [III] or a salt thereof, which can be used as the starting material for the method of this invention as it is or after isolation and purification by the above-mentioned per se known means.

The other starting compound [II] can be synthesized by the method disclosed in, for example, U.S. Pat. No. 3,066,140, etc. or by analogous methods thereto, the compounds [VIII] and [X] or salts thereof can be synthesized by methods disclosed in, for example, "Chemical Abstracts", 70, 87705a (1969) and 73, 14776b (1970); "Organic Functional Group Preparations", Vol. 1, p. 270 to 300 (1968), etc., or by analogous methods thereto, the compound [IX] can be synthesized by the method disclosed in, for example, "Organic Functional Group Preparations, Vol. 1, p. 117 to 145 (1968), etc. or by analogous methods thereto, and the compound [XI] can be synthesized by the method disclosed in, for example, "Chemical Abstracts", 66, 85678n (1967), etc. or by analogous methods thereto.

The compound [III] or a salt thereof can be produced by the following reaction scheme.

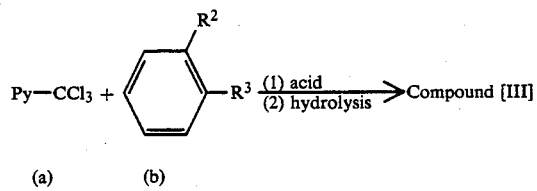

(a)   (b)

wherein the symbols are as defined above.

The compound [III] or a salt thereof can be produced by reacting the compound (a) with the compound (b) in the presence of acid, and then hydrolyzing the resulting compound.

As the acid, use is made of Lewis acid. Examples of the Lewis acid include zinc chloride, zinc bromide, ferric chloride, ferric bromide, stannic chloride and antimony chloride. The acid is preferably used in an amount of about 1 to 5 moles per 1 mole of the compound (a).

The compound (b) is used in an amount of about 1 to 5 moles per 1 mole of the compound (a).

The reaction is usually conducted in a solvent. Examples of the solvent include aliphatic hydrocarbons such as hexane, heptane or decalin; halogenated hydrocarbons such as dichloromethane, chloroform, carbon tetrachloride, 1,2-dichloroethane, 1,1,1-trichloroethane or chlorobenzene; ethers such as diethyl ether, diisopropyl ether, tetrahydrofuran, dioxane, 1,2-dimethoxyethane or diphenyl ether; ketones such as acetone, ethyl methyl ketone or isopropyl methyl ketone; acetonitrile, nitrobenzene, dimethylsulfoxide and amides such as dimethylformamide or dimethylacetamide. The solvent may be used singly or as the mixture thereof.

The reaction temperature is about 20° C. to 100° C. The reaction time is about 30 minutes to 30 hours.

The resultant compound in the reaction mixture is hydrolyzed. The hydrolysis is conducted by adding water or water containing a mineral acid to the reaction mixture. Examples of the mineral acid include hydrochloric acid, sulfuric acid and nitric acid. The reaction temperature is about 10° C. to 100° C. The reaction time is about 10 minutes to 10 hours.

The compound obtained can be used after isolating and purifying by the above-mentioned cer se known means, or as the reaction mixture itself.

The novel compound [I] or a salt thereof exhibits excellent preventing and controlling effects against plant diseases, e.g. downy mildew or late blight of vegetables or fruits, and the present invention serves to decrease injuries due to disease of vegetables or fruits.

The compound [I] or a salt thereof shows excellent rain-resistance effect, because of little washing off by rain after application by spraying and exerts sufficient effects even in the rainy season.

TEST EXAMPLE 1

Test of Preventing Effect against Late Blight of Tomato

The compound of the present invention was dissolved in dimethylformamide (final concentration: 1 weight %), to which were added xylene (final concentration: 0.02 weight %) and Tween 20 ® (final concentration: 0.02 weight followed by diluting with tap water so as to adjust the concentration of the effective component to be the given one. To the solution was added a spreader, Dyne (manufactured by Takeda Chemical Industries, Ltd., containing 20 weight % of polyoxyethylene nonyl phenol ether and 12 weight % of calcium lignin sulfonate) at a rate of 0.05 weight % (final concentration) to prepare a spray-solution. The solution was sprayed on young tomato seedlings (about 4-weeks) sufficiently to the extent of its dripping off the seedlings. After air-drying, the seedlings were inoculated with a suspension of sporangia $Phytophthora\ infestans$ (concentration: about $10^5$/ml) by spraying. Thus-sprayed seedlings were kept for 5 days in a green house under high humidity condition at 17° C., then the ratio of affected area of each seedling was examined. Protecting and controlling values are shown by the following coefficients.

Protecting and controlling value 3: Affected surface area ratio 0 to 5%
Protecting and controlling value 2: Affected surface area ratio 6 to 15%
Protecting and controlling value 1: Affected surface area ratio 16 to 30%
Protecting and controlling value 0: Affected surface area ratio not less than 31%

The results are shown in Table 1.

TEST EXAMPLE 2

Test of Preventing Effect against Downy Mildew of Cucumber

A spray-solution containing a compound of the present invention at a given concentration was prepared by the method described in Test Example 1. The solution was sprayed on young cucumber seedlings (about 3-weeks) sufficiently to cause its dripping off the seedlings. After air-drying, the seedlings were inoculated with a suspension of sporangia of *Pseudoperonospora cubensis* (concentration: about $10^5$/ml) by spraying. Thus-sprayed seedlings were kept for one day in a green house under highly humid condition at 20° C., then for six days in a green house. The ratio of affected area of each seedling was examined. Preventing and controlling values are shown by the following coefficients.

Protecting and controlling value 3: Affected surface area ratio 0 to 5%
Protecting and controlling value 2: Affected surface area ratio 6 to 15%
Protecting and controlling value 1: Affected surface area ratio 16 to 30%
Protecting and controlling value o: Affected surface area ratio not less than 31%

The results are shown in Table 1.

TEST EXAMPLE 3

Downy Mildew of Cucumber, Rain-Resistance Test

A spray-solution containing a compound of the present invention at a given ratio was prepared in accordance with the method described in Test Example 1. The solution was sprayed on young cucumber seedlings (about 3-weeks) sufficiently to cause its dripping off the seedlings. One day after the spraying, test seedlings were exposed to artificial rain at a rate of 30 mm/hour, then air-dried, followed by inoculation with a suspension of sporangia of *Pseudoperonospora cubensis* (concentration: about $10^5$/ml) by spraying. Thus-sprayed seedlings were kept for one day in a green house at 20° C., then for six days in a green house. The ratio (%) of the affected area of each seedling was examined. The results are shown in Table 2.

TABLE 1

Preventing and Controlling Effects against Late Blight of Tomato and Downy Mildew of Cucumber

| Test Compound | Late Blight of Tomato 200 ppm | Downy Mildew of Cucumber 200 ppm |
|---|---|---|
| 1 | 3 | 3 |
| 2 | 3 | 3 |
| 3 | 3 | 3 |
| 4 | 3 | 3 |
| 5 | 3 | 3 |
| 6 | 3 | 3 |
| 8 | 3 | 3 |
| 9 | 3 | 3 |
| 11 | 3 | 3 |
| 12 | 3 | 3 |
| 16 | 3 | 3 |
| 18 | 3 | 3 |
| 20 | 3 | 3 |
| 22 | 3 | 3 |
| 23 | 3 | 3 |
| 24 | 3 | 3 |
| 25 | 3 | 3 |
| 27 | 3 | 3 |
| 33 | 3 | 3 |
| 34 | 3 | 3 |
| 36 | 3 | 3 |
| 39 | 3 | 3 |
| 41 | 3 | 3 |
| 42 | 3 | 3 |
| 48 | 3 | 3 |
| 49 | 3 | 3 |
| 50 | 3 | 3 |
| 51 | 3 | 3 |
| 52 | 3 | 3 |
| 54 | 3 | 3 |
| 57 | 3 | 3 |
| 58 | 3 | 3 |
| 59 | 3 | 3 |
| 62 | 3 | 3 |
| 63 | 3 | 3 |
| 66 | 3 | 3 |
| 71 | 3 | 3 |
| 72 | 3 | 3 |
| 82 | 3 | 3 |
| 84 | 3 | 3 |
| 86 | 3 | 3 |
| 88 | 3 | 3 |
| 89 | 3 | 3 |
| 92 | 3 | 3 |
| 97 | 3 | 3 |
| 100 | 3 | 3 |
| 101 | 3 | 3 |
| 103 | 3 | 3 |
| 104 | 3 | 3 |
| 106 | 3 | 3 |
| 107 | 3 | 3 |
| 108 | 3 | 3 |
| 109 | 3 | 3 |
| 110 | 3 | 3 |
| 111 | 3 | 3 |
| 112 | 3 | 3 |
| 113 | 3 | 3 |
| Comparative Compound | | |
| Manzeb | 0 | 0 |
| A | 0 | 0 |

TABLE 2

Preventing and Controlling Effects against Downy Mildew of Cucumber (Rain-Resistance Test)

| Test Compound | Concentration of Spray-Solution (ppm) 100 | 50 |
|---|---|---|
| 3 | 0 | 0 |
| 4 | 7 | 12 |
| 6 | 0 | 2 |
| 11 | 0 | 0.3 |
| 12 | 0 | 0 |
| 27 | 0 | 0 |
| 33 | 0 | 0 |
| 34 | 0.3 | 1 |
| 42 | 0 | 0.3 |
| 48 | 0 | 0 |
| 50 | 0.7 | 3.7 |

TABLE 2-continued

Preventing and Controlling Effects against Downy Mildew of Cucumber (Rain-Resistance Test)

| Test Compound | Concentration of Spray-Solution (ppm) | |
|---|---|---|
| | 100 | 50 |
| 58 | 0 | 0 |
| 82 | 0 | 1.7 |
| 86 | 0 | 0 |
| 88 | 0 | 0 |
| 106 | 0 | 0 |
| 108 | 0 | 1 |
| 110 | 0 | 0 |
| Comparative Compound | | |
| TPN | 23 | 37 |
| A | 100 | 100 |

In the above Tables 1 and 2, the number in the column of "Test Compounds" corresponds to the Compound No. synthesized in the following Examples. The comparative compound "TPN" in Table 2 is a commercially available fungicide, tetrachloroisophthalonitrile. The comparative compound A is represented by the formula:

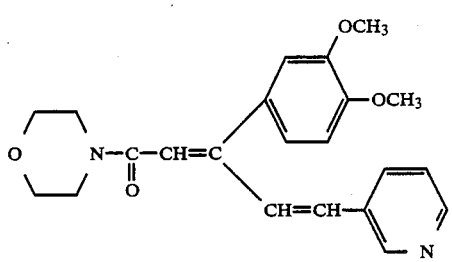

described in Example 77 of EP-A-120321.

The above Tables 1 and 2 evidently prove that the object compound [I] of the present invention exerts preventing and controlling effects against late blight and downy mildew superior to commercially available agricultural chemicals and structurally analogous known compounds and that these effects are resistant against rain.

The following Reference Examples and Examples are intended to illustrate the present invention in further detail, but they should by no means be construed as limiting the scope of the present invention.

Elution in the column chromatography in the Reference Examples and Examples was conducted under observation by means of Thin Layer chromatography (TLC). In the TLC observation, Kieselgel 60F$_{254}$ (Art.5715) manufactured by E. Merck AG was employed as TLC plate, the solvent used as eluent for the column chromatography was employed as developing agent, and a UV detector was employed as detecting means. The silica gel used for the column was Kieselgel 60(70 to 230 mesh, Art.7734) manufactured by E. Merck AG. NMR spectra show proton NMR determined by, unless otherwise specified, a VARIAN EM 390 (90 MHz) type spectrometer, employing tetramethylsilane as the internal or external standard, and all the δ values were shown in terms of ppm. In the case of using a mixed solvent as the developing solvent, numerical values shown with parentheses mean the volumetric ratio of the respective solvents.

Symbols used in Reference Examples and Examples have the following meaning.

Me: methyl group, s: singlet, d: doublet,
dt: doublet triplet, dd: doublet doublet,
t: triplet, q: quartet, m: multiplet,
J: coupling constant, Hz: hertz, DMSO-d$_6$: deuterio DMSO (dimethylsulfoxide), %: weight %

And, the term "room temperature" means the range from about 15° C. to 25° C.

REFERENCE EXAMPLE 1

(Method A)

To 200 ml of tetrahydrofuran were added metallic magnesium (5.35 g) and 4-bromoveratrole (47.8 g), and the mixture was heated for 3 hours under reflux to prepare a 3,4-dimethoxyphenyl magnesium bromide solution. This solution was added, while stirring, dropwise at temperatures ranging from −50° C. to −60° C. to a solution of 6-chloronicotinic acid chloride (21.2 g) in tetrahydrofuran (200 ml) (the time required for the addition: one hour). The resultant mixture was stirred at the same temperature for 2 hours and 40 minutes, and there was then added 2N hydrochloric acid (100 ml). Precipitating crystals were collected by filtration, washed with water and dried to afford 2-chloro-5-(3,4-dimethoxybenzoyl)pyridine (22.5 g), m.p. 158° to 159° C.

NMR (CDCl$_3$+DMSO-d$_6$) δppm: 3.93 (3H, s), 3.97 (3H, s), 6.97 (1 H, d, J=9 Hz), 7.37 (1 H, d, d, J=9 Hz, 1.5 Hz), 7.43 (1 H, s), 7.50 (1 H, d, J=9 Hz), 8.08 (1 H, d, d, J=9 Hz, 1.5 Hz), 8.70 (1 H, d, J=1.5 Hz)

(Method B)

In 11 ml of nitrobenzene were dissolved 0.69 g of 2-chloro-5-trichloromethylpyridine and 0.62 g of veratrole, to which 1 g of zinc chloride and 0.3 ml of dimethylformamide were added with stirring. After stirring at 70° C. for 12 hours, 10 ml 1N HCl was added to the reaction mixture, and the mixture was stirred at 50° to 60° C. for 30 minutes.

After cooling to room temperature, the reaction mixture was extracted with dichloromethane. The extracts were dried over anhydrous magnesium sulfate, and concentrated.

The residue was purified by silicagel column chromatography [eluted with a mixture solvent of dichloromethane and diethyl ether (10:1)], to give 0.56 g of 2-chloro-5-(3,4-dimethoxybenzoyl)pyridine mp 158°–159° C.

REFERENCE EXAMPLE 2

In dimethyl formamide (10 ml) was suspended 60% sodium hydride (dispersion in paraffin) (288 mg), to which was added dropwise a solution of 2-chlorophenol (926 mg) in dimethylformamide. When exothermic reaction and evolution of hydrogen gas ceased, 2-chloro-5-(3,4-dimethoxybenzoyl)pyridine (1 g) was added to the reaction mixture, followed by stirring for hours at 80° C. The reaction mixture was poured into ice-water, then precipitating substance was collected by filtration, and purified by means of a silica gel column chromatography [eluent: n-hexane+ethyl acetate (1:1)] to obtain 2-(2-chlorophenoxy)-5-(3,4-dimethoxybenzoyl)pyridine (1.1 g) as an oil.

NMR (CDCl$_3$) δ ppm: 3.97 (6 H, s), 6.87 to 7.60 (8 H, m), 8.23 (1 H, d, d, J=9 Hz, J=3 Hz), 8.57 (1 H, d, J=3 Hz)

In like manner, the following compounds were synthesized.

5-(3,4-dimethoxybenzoyl)-2-(2,3,5,6-tetrafluorophenoxy)pyridine: m.p. 116° to 117° C.

NMR (CDC13) δ ppm: 3.97 (6 H, s), 6.87 to 7.50 (5 H, m), 8.27 (1 H, dd, J=9 Hz, J=3 Hz), 8.52 (1 H, d, J=3 Hz)

5-(3,4-dimethoxybenzoyl)-2-(2,6-dichlorophenoxy)pyridine: m.p. 133° to 134° C.

NMR (CDCl3) δ ppm: 3.96 (6 H, s), 6.82 to 7.50 (7 H, m), 8.22 (1 H, dd, J=8 Hz, J=2 Hz), 8.52 (1 H, d, J=2 Hz)

5-(3,4-dimethoxybenzoyl)-2-(4-trifluoromethyl phenoxy)-pyridine: oil

NMR (CDC13) δ ppm: 3.97 (6 H, s), 6.92 (1 H, d, J=9 Hz), 7.12 (1 H, d, J=9 Hz), 7.23 to 7.53 (4 H, m), 7.73 (1 H, d, J=9 Hz), 8.23 (1 H, d, J=9 Hz), 8.27 (1 H, d, J=3 Hz)

2-(4-chlorophenoxy)-5-(3,4-dimethoxybenzoyl)pyridine: m.p. 129° to 131° C.

NMR (CDC13) δ ppm: 3.97 (6 H, s), 6.84 to 7.53 (8 H, m), 8.21 (1 H, d, d), 8.59 (1 H, d)

2-(4-chloro-2-fluorophenoxy)-5-(3,4-dimethoxybenzoyl)pyridine: oil

NMR (CDCl3) δ ppm: 3.97 (6 H, s), 6.83 to 7.50 (7 H, m), 8.22 (1 H, d, d), 8.53 (1 H, d)

2-(4-bromo-2-fluorophenoxy)-5-(3,4-dimethoxybenzoyl)pyridine: oil

NMR (CDC13) δ ppm : 3.97 (6 H, s), 6.83 to 7.53 (7 H, m), 8.22 (1 H, d, d), 8.53 (1 H, d)

2-(2-chloro-4-trifluoromethylphenoxy)-5-(3,4-dimethoxybenzoyl)pyridine: oil

NMR (CDCl3) δ ppm: 3.97 (6 H, s), 6.80 to 7.80 (7 H, m), 8.25 (1 H, d, d), 8.55 (1 H, d)

2-(2-chloro-4-fluorophenoxy)-5-(3,4-dimethoxybenzoyl)pyridine: oil

NMR (CDCl3) δ ppm: 3.97 (6 H, s), 6.83 to 7.50 (7 H, m), 8.22 (1 H, d, d), 8.55 (1 H, d)

2-(2-phenylethyl)-5-(3,4-dimethoxybenzoyl)pyridine: m.p. 95° to 99° C.

NMR (CDCl3) δ ppm: 3.03 to 3.26 (4 H, m), 3.96 (3 H, s), 3.98 (3H, s), 6.93 (1 H, d), 7.10 to 7.58 (8 H, m), 8.00 (1 H, d, d), 8.95 (1 H, d)

2-(4-chloro-3-fluorophenoxy)-5-(3,4-dimethoxybenzoyl)pyridine: oil

NMR (CDCl3) δ ppm: 3.95 (6H, d), 6.50-7.55 (7H, m), 8.17 and 8.27 (1H, d,d), 8.56 (1H, d)

2-(4-methoxy-3-fluorophenoxy)-5-(3,4-dimethoxybenzoyl)pyridine m.p. 98° to 100° C.

2-(4-chloro-2,3-difluorophenoxy)-5-(3,4-dimethoxybenzoyl)pyridine: oil

NMR (CDCl3) δ ppm: 3.96 (6H, d), 6.80-7.55 (6H, m), 8.18 and 8.28 (1H, d,d), 8.56 (lH, d)

2-(4-chloro-2,6-difluorophenoxy)-5-(3,4-dimethoxybenzoyl)pyridine: oil

NMR (CDCl3) δ ppm: 3.95 (6H, S), 6.83-7.50 (6H, m), 8.22 (1H, dd), 8.53 (1H, d)

2-(2-chloro-4,6-difluorophenoxy)-5-(3,4-dimethoxybenzoyl)pyridine: oil

NMR (CDCl3) δ ppm: 4.00 (6H, s), 6.93 (1H, d), 7.27-7.59 (5H, m) 8.17 (1H, dd), 8.77 (1H, d)

2-(2-bromo-5-fluorophenoxy)-5-(3,4-dimethoxybenzoyl)pyridine: oil

NMR (CDCl3) δ ppm: 4.00 (6H, s), 6.94 (1H, d), 7.27-7.61 (6H, m), 8.15 (1H, dd), 8.78 (1H, d)

2-(4-bromo-2-chloro-6-fluorophenoxy)-5-(3,4-dimethoxybenzoyl)pyridine: oil

NMR (CDCl3) δ ppm: 3.97 (6H, s), 6.91 (1H, d), 7.11-7.53 (5H, m), 8.19 and 8.29 (1H, d,d), 8.51 (1H, d)

2-(4-bromo-2,4-difluorophenoxy)-5-(3,4-dimethoxybenzoyl)pyridine: m.p. 158°-160° C.

2-(4-bromo-2-chloro-phenoxy)-5-(3,4-dimethoxybenzoyl)pyridine: oil

NMR (CDCl3) δ ppm: 3.95 (3H, s), 3.98 (3H, s), 6.98 (1H, d), 7.20 - 7.70 (6H, m), 8.10 (1H, dd), 8.77 (1H, d)

2-(4-bromo-2-methyphenoxy)-5-(3,4-dimethoxybenzoyl)pyridine: m.p. 118°-119° C.

2-(4-bromo-2-methyphenoxy)-5-(3,4-dimethoxybenzoyl)pyridine: m.p. 108°-111° C.

2-(4-bromo-3-methoxyphenoxy)-5-(3,4-dimethoxybenzoyl)pyridine: oil

NMR (CDCl3) δ ppm: 3.89 (3H, S), 3.97 (6H, S), 6.83-7.57 (6H, m), 8.23 (1H, dd), 8.57 (1H, d)

2-(2-chlorobehzyl)-5-(3,4-dimethoxybenzoyl)pyridine: m.p. 98°-100° C.

2-(2-chlorobenzylthio)-5-(3,4-dimethoxybenzoyl)pyridine: m.p. 108°-109° C.

2-(2,3,5,6-tetrafluorophenylthio)-5-(3,4-dimethoxybenzoyl)pyridine: m.p. 135°-137° C.

REFERENCE EXAMPLE 3

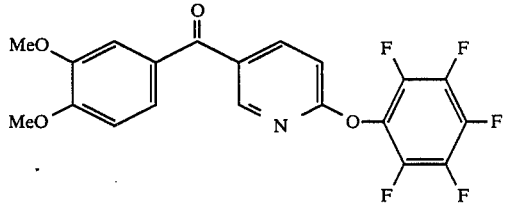

In dimethylformamide (10 ml) was suspended 60% sodium hydride (dispersion in paraffin) (288 mg), to which was added dropwise a solution of pentafluorophenol [1.3 g (7.2 mmol.)] in dimethylformamide (10 ml). When exothermic reaction and evolution of hydrogen gas ceased, 2-chloro-5-(3,4-dimethoxybenzoyl)pyridine (1 g) and cuprous iodide (69 mg) were added to the reaction mixture, followed by stirring for 5 hours under reflux. The reaction mixture was poured into ice-water, which was subjected to extraction with dichloromethane. The organic layer was washed with water, dried over anhydrous magnesium sulfate, and then concentrated under reduced pressure. The concentrate was purified by means of a silica gel column chromatography [eluent: n-hexane+ethyl acetate (3:1)] to obtain 5-(3,4-di-methoxybenzoyl)-2-pentafluorophenoxypyridine (900 mg) as white crystals, m.p. 107° to 109° C.

NMR (CDCl3) δ ppm: 3.97 (6 H, s), 6.93 (1 H, d, J=9 Hz), 7.20 to 7.53 (3 H, m), 8.27 (1 H, dd, J=9 Hz, 3 Hz), 8.50 (1H, J=3 Hz)

REFERENCE EXAMPLE 4

In dimethylformamide (30 ml) was dissolved N-methylaniline (1.2 g). To the solution was added 60% sodium hydride (dispersion in praraffin) (150 mg), and the mixture was stirred for 30 minutes. Then there was added 2-chloro-5-(3,4-dimethoxybenzoyl)pyridine (500 mg). The mixture was stirred for 4 hours at 90° C. The reaction mixture was poured into ice-water, which was subjected to extraction with dichloromethane. The organic layer was washed with water, dried over anhydrous sodium sulfate and concentrated under reduced pressure. The concentrate was purified by means of a silica gel column chromatography (eluent: n-hexane +ethyl acetate=2:1) to obtain 5-(3,4-dimethoxybenzoyl)-2-(N-methylanilino)pyridine (200 mg) as an oil.

NMR (CDCl$_3$) δ ppm: 3.60 (3 H, s), 3.93 (6H, s), 6.50 (1 H, d), 6.90 (1H,d), 7.17 to 7.67 (7H, m), 7.83 (1 H, d, d), 8.70 (1 H, d)

REFERENCE EXAMPLE 5

60% Sodium hydride (dispersion in paraffin) was washed with pentane and dried under an atmosphere of nitrogen gas, and there added 1,2-dimethoxyethane (200 To the mixture was added a solution of diethylphosphonoacetic acid morphoride (27.3 g) in 1,2-dimethoxyethane (20 ml) dropwise at 20° to 23° C. The resultant mixture was stirred for 20 further minutes, and there was added 2-chloro-5-(3,4-dimethoxybenzoyl)pyridine (27.7g), followed by heating for 4 hours under reflux. The reaction mixture was concentrated, and the concentrate was dissolved in dichloromethane, then the solution was washed with water. The dichloromethane layer was concentrated under reduced pressure. The concentrate was purified by means of a silica gel column chromatography (eluted with ethyl acetate) to obtain 4-[3-(2-chloro-5-pyridyl)-3-(3,4-dimethoxyphenyl)acryloyl]morpholine (30.3 g), m.p. 154° to 160° C.

From NMR data, it was found that this crystalline product was a mixture of E-isomer and Z-isomer (about 1:5).

NMR (CDCl$_3$) δ ppm: 3.07 to 3.67 (8 H, m), 3.83 (3 H, s), 3.90 (3 H, s), 6.25 and 6.43 (1 H, s and s, E-isomer and Z-isomer), 6.67 to 6.93 (3 H, m), 7.33 (1 H, d), 7.47 to 7.67 (1 H, m), 8.28 and and Z-isomer) 8.38 (1H, d and d, E-isomer

REFERENCE EXAMPLE 6

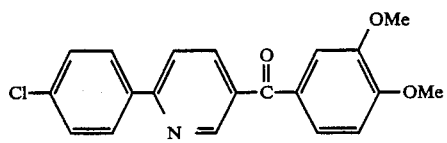

In dry tetrahydrofuran (10 ml) was dissolved 4-bromoveratrol (1.2 g). To the solution was added dropwise slowly an n-hexane solution (3.7 ml) of 15% n-butyllithium, while stirring under cooling at −68° C. to −70° C. under an atmosphere of nitrogen gas. The mixture was stirred for 20 minutes at the same temperature range for 20 minutes. Then there was added dropwise in the course of 30 minutes a solution of 2-(4-chlorophenyl)-5-cyanopyridine (0.8 g) in dry tetrahydrofuran (8 ml). The mixture was stirred at the same temperature range for 30 minutes, followed by addition of methanol (6 ml), and warming to the room temperature, slowly. The reaction mixture was concentrated, and there was added ethyl acetate (100 ml), and the solution was washed with ice-water (30 ml) once, to which was added silica gel (60 g), followed by stirring at room temperatures for 2 hours. The reaction mixture was then left standing overnight, and the silica gel was filtered off. To the filtrate was added anhydrous magnesium sulfate for drying, and the filtrate was subjected to filtration. The filtrate was concentrated, and the concentrate was purified by means of a silica gel chromatography (eluted with chloroform), followed by recrystallization from acetonitrile to obtain 2-(4-chlorophenyl)-5-(3,4-dimethoxybenzoyl)pridine (700 mg) as pale yellow granular crystals, m.p. 168° to 170° C.

NMR(CDCl$_3$) δ ppm: 3.96 (3 H, s), 3.98 (3 H, s), 6.93 (1 H, d, J=9.0 Hz), 7.27 to 7.60 (4 H, m), 7.82 (1 H, d, J=9.0 Hz), 7.97 to 8.26 (3 H, m), 9.00 to 9.11 (1 H, m)

REFERENCE EXAMPLE 7

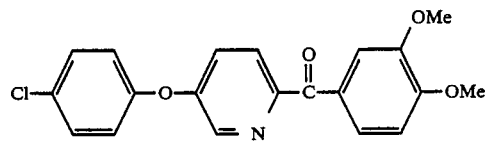

In anhydrous tetrahydrofuran (6 ml) was dissolved 4-bromoveratrol (700 mg). To the solution was added dropwise a 15% n-hexane solution of n-butyllithium (2.2 ml), while stirring under cooling at temperatures ranging from −60° C. to −70° C. under an atmosphere of nitrogen gas. The mixture was stirred at the same temperature range for 20 minutes, and there was added dropwise at temperatures of −70° C. or below a solution of 5-(4-chlorophenoxy)-2-cyanopyridine (500 mg) in dry tetrahydrofuran (6 ml). The mixture was stirred at the same temperature for 30 minutes, and there was added methanol (1 ml) (the temperature rose up to −65° C. from −73° C.), then the temperature of the mixture was slowly warmed to room temperature. To the reaction mixture was added silica gel (3 g), and there was then added water (0.5 ml), and the mixture was stirred at room temperature for 2 hours, and left standing overnight. Silica gel was filtered off, and the filtrate was concentrated. The concentrate was purified by means of a silica gel column chromatography [eluted with a mixture solvent of dichloromethane and ethyl acetate (10:1)] to obtain 5-(4-chloro-phenoxy)-2-(3,4-dimethoxybenzoyl)pyridine (240 mg) as colorless crystals, m.p. 145 to 147° C.

NMR(CDCl$_3$) δ ppm: 3.98 (6 H, s), 6.89 to 7.20 (3 H, m), 7.28 to 7.53 (3 H, m), 7.73 to 8.16 (3 H, m), 8.48 (1 H, d, J=3 Hz)

REFERENCE EXAMPLE 8

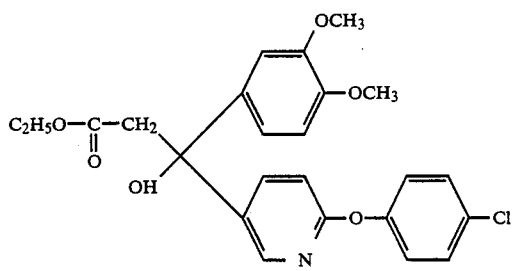

0.7 g of Zinc powder were suspended in 10 ml of benzene, to which was added 0.1 ml of chlorotrimethylsilane, and the mixture was stirred for 15 minutes at room temperature and for 20 minutes at 50° C. After cooling to the room temperature, there were added 1.4 g of ethyl bromoacetate to the mixture, followed by stirring for 15 minutes.

2.4 g of 2-(4-chlorophenoxy)-5-(3,4-dimethoxybenzoyl)pyridine were added in a small portion to the mixture and refluxed for 20 minutes. The reaction mixture was cooled to the room temperature and insoluble matters were removed by filtration and the resultant filtrate was concentrated. The residue was purified by silica gel column chromatography to give 2.48 g of ethyl 3-[2-(4- chlorophenoxy)-5-pyridyl]-3-(3,4-dimethoxyphenyl)-3-hydroxypropionate as a pale yellow, viscous oil.

Yield: 83.5 %

NMR (CC14) δ ppm: 1.18 (3H, t, J=7.5Hz), 3.10 (2H, s), 3.80 (6H, s), 4.10 (2H, q, J=7.5 Hz), 5.10 (1H, s), 6.69 - 6.90 (3H, m), 6.95-7.14 (3H, m), 7.22-7.40 (2H, m), 7.71 (1H, dd, J=3.0 Hz and 9.0 Hz), 8.02 (1H, d, J=3.0 Hz).

REFERENCE EXAMPLE 9

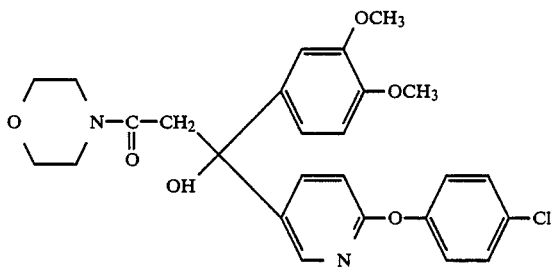

1.6 g of ethyl 3-[2-(4-chlorophenoxy)-5-pyridyl]-(3,4-dimethoxyphenyl)-3-hydroxypropionate was dissolved in 12 ml of morpholine, to which were added 5 drops of 45 % boron trifluoride diethyl ether complex, followed by reflux for 5 hours.

The reaction mixture was evaporated and the residue was dissolved in ethyl acetate. The mixture was washed with water, dried over anhydrous magnesium sulfate and concentrated. The residue was purified by silicagel column chromatography (eluent: ethyl acetate) to give 1.18 g of 3-[2-(4-chlorophenoxy)-5-pyridyl]-3-(3,4-dimethoxyphenyl)-3-hydroxypropionic acid morpholide as a viscous oil.

NMR (CC14) δ ppm: 3.00 (2H, s), 3.29-3.67 (8H, m), 3.78 (3H, s), 3.80 (3H, s), 6.38 (1H, s), 6.51-6.71 (2H, m), 6.74-6.90 (1H, m), 6.95-7.41 (5H, m), 7.77 (1H, dd, J=3.0 and 9.0 Hz), 7.96 (1H, d, J=3.0 Hz).

EXAMPLE 1

In 1,2-dimethoxyethane (10 ml) was suspended 60% sodium hydride (dispersion in paraffin) (132 mg). To the suspension was added dropwise, while stirring, a solution of diethylphosphonoacetic acid morpholide (688 mg) in 1,2-dimethoxyethane (5 ml). To the mixture was added 2-(2-chlorophenoxy)-5-(3,4-dimethoxybenzoyl)-pyridine (800 mg), which was heated for 8 hours under reflux. The reaction mixture was concentrated and the residue was dissolved in ether, washed with water and dried over anhydrous magnesium sulfate. The solvent was then distilled off to leave an oily substance, which was purified by means of a silica gel chromatography (eluted with ethyl acetate) to obtain 4-[3-(2-(2-chlorophenoxy)-5-pyridyl]-3-(3,4-dimethoxyphenyl)acryloyl]morpholine (Compound No.1) (330 mg) as a resinous solid.

From NMR data, it was found that this substance was a mixture of E-isomer and Z-isomer (about 2:3).

NMR (CDCl3) δ ppm: 3.00 to 3.73 (8 H, m), 3.83 (3 H, s), 3.90 (3 H, s), 6.20 and 6.30 (1H, s,s, E-isomer and Z-isomer), 6.67 to 7.70 (9 H, m), 8.00 to 8.20 (1H, m)

EXAMPLE 2

Method A

In dimethylformamide (20 ml) was dissolved 4-chlorophenol (330 mg). To the solution was added, while stirring, 60% sodium hydride (dispersion in paraffin) (103 mg). When exothermic reaction and evolution of hydrogen gas ceased, 4-[3-(2-chloro-5-pyridyl)-3-(3,4-dimethoxyphenyl)acryloyl]morpholine (500 mg) and cuprous iodide (24 mg) were added to the reaction mixture, followed by stirring for 5 hours at 150° C. The reaction mixture was poured into water, which was subjected to extraction with dichloromethane. The extract solution was dried over anhydrous magnesium sulfate, which was then concentrated. The concentrate was purified by means of a silica gel column chromatography (eluted with ethyl acetate) to obtain 4-[3-(2-(4-chlorophenoxy)-5-pyridyl)-3-(3,4-dimethoxyphenyl)acryloyl]morpholine (Compound No. 3 ) (420 mg) as a resinous solid.

From NMR data, it was found that this substance was a mixture of E-isomer and Z-isomer (about 2:3).

NMR(CDCl3) δ ppm: 3.00 to 3.70 (8 H, m), 3.83 (3 H, s), 3.85 (3 H, s), 6.20 and 6.33 (1 H, s, E-isomer and Z-isomer), 6.67 to 7.67 (9 H, m), 8.07, 8.17 (1 H, dd; E-isomer and Z-isomer).

Method B 2.8 g of 3-[2-(4-chlorophenoxy)-5-pyridyl]-3-(3,4-dimethoxyhenyl)-3-hydroxypriopionic acid morpholide were dissolved in 10 ml of acetic acid, followed by reflux for 2 hours.

The reaction mixture was concentrated under reduced pressure, and the residue was dissolved in ethyl acetate.

The mixture was washed with water, 10% aqueous sodium hydrogen carbonate and water in that order, and dried over anhydrous magnesium sulfate. After concentration, the residue was purified by silicagel column chromatography (eluent: ethyl acetate) to give 2.6 g of 4-[3-(2-(4-chlorophenoxy)-5-pyridyl)-3-(3,4-dimethoxyphenylacryloyl]morpholine.

NMR spectrum was confirmed to be identical with that described above.

EXAMPLE 3

In the same manner as in Example 2, using 4-chlorothiophenol (1.1 g), 4-[3-(2-chloro-5-pyridyl)-3-(3,4-dimethoxyphenyl)acryloyl]morpholine (1 g) and 60% sodium hydride (312 mg), 4-[3-(2-(4-chlorophenylthio)-5-pyridyl-3-(3,4-dimethyoxyphenyl)acryloyl]morpholine (Compound No. 59) (0.72 g), was obtained.

m.p. 61° to 64° C.

From NMR data, it was found that this substance was a mixture of E-isomer and Z-isomer (about 1:1).

NMR (CDCl3) δ ppm: 3.00 to 3.67 (8 H, m), 3.70, 3.83 and 3.90 (6 H, s, s, s), 6.22 and 6.35 (1 H, s,s; E-isomer and Z-isomer), 6.67 to 7.00 (4 H, m, 7.30 to 7.67 (5 H, m), 8.30 and 8.42 (1 H, d, d; E-isomer and Z-isomer)

EXAMPLE 4

In the same manner as in Example 2, using benzyl alcohol (554 mg), 4-[3-(2-chloro-5-pyridyl)-3-(3,4-dimethoxyphenyl)acryloyl]morpholine (1 g) and 60% sodium hydride (205 mg), 4-[3-(2-benzyloxy-5-pyridyl)-3-(3,4-dimethoxyphenyl)acryloyl]morpholine (Compound No.63) (0.9 g) was obtained as a resinous solid.

Form NMR data, it was found that this substance was a mixture of E-isomer and Z-isomer (about 4:3).

NMR(CDCl3) δ ppm: 3.03 to 3.70 (8 H, m), 3.87 (6 H, s), 5.42 (2 H, s), 6.17 and 6.27 (1 H, s, s; E-isomer and Z-isomer), 6.70 to 6.93 (3 H, m), 7.27 to 7.60 (7 H, m), 8.10 and 8.17 (1 H, d, d; E-isomer and Z-isomer)

EXAMPLE 5

In the same manner as in Example 1, using 5-(3,4-dimethoxybenzoyl)-2-(N-methylanilino)pyridine (500 mg), diethylphosphonoacetic acid morpholide (800 mg) and 60% sodium hydride (150 mg), E-isomer (250 mg) and Z-isomer (212 mg) of 4-[3-(2-(N-methylanilino)-5-pyridyl)-3-(3,4-dimethoxyphenyl)acryloyl]morpholine (Compound No.62) were obtained.

NMR (CDCl$_3$) δ ppm: E-isomer—3.3 to 3.6 (8 H, m), 3.18 (3 H, s), 3.83 (3 H, s), 3.86 (3 H, s), 6.19 (1 H, s), 6.50 (1 H, s), 6.81 (2 H, s), 7.25 to 8.20 (9 H, m) Z-isomer—3.3 to 3.6 (8 H, m), 3.17 (3 H, s), 3.83 (3 H, s), 3.86 (3 H, s), 6.17 (1 H, s), 6.50 (1 H, s), 6.83 (2 H, s), 7.25 to 8.10 (9 H, m)

EXAMPLE 6

In the same manner as in Example 1, using 2-(4-chlorophenyl)-5-(3,4-dimethoxybenzoyl)-pyridine (700 mg), diethylphosphonoacetic acid morpholide (630 mg) and 60% sodium hydride (95 mg), 4-[3-(2-(4-chlorophenyl)-5-pyridyl)-3-(3,4-dimethoxyphenyl)acryloyl]-morpholine (Compound No. 82) (690 mg) was obtained as a resinous solid.

From NMR data, it was found that this substance was a mixture of E-isomer and Z-isomer (about 4:7).

NMR (CDCl$_3$) δ ppm: 2.10 to 3.78 (8 H, m), 3.82 to 4.01 (6 H, m), 6.37 and 6.47 (1 H, s·s, E-isomer and Z-isomer), 6.86 to 7.01 (3 H, m), 7.42 to 7.61 (2 H, m), 7.68 to 7.88 (2 H, m), 7.93 to 8.15 (2 H, m), 8.58 to 8.79 (1 H, m)

EXAMPLE 7

In 1,2-dimethoxyethane (10 ml) was dissolved diethylphosphonoacetic acid morpholide (210 mg), to which was added 90% potassium tert-butoxide (100 mg). To the mixture was added, after the tert-butoxy potassium was completely dissolved, 5-(4-chlorophenoxy)-2-(3,4-dimethoxybenzoyl)pyridine (240 mg). The mixture was stirred for one hour at room temperature and for 6 hours at 50° C. to 60° C. The reaction mixture was concentrated, and there was added water (30 ml), followed by extraction with ethyl acetate (70 ml×2). The extract solution was dried over anhydrous magnesium sulfate, and was subjected to filtration to remove the magnesium sulfate. The filtrate was concentrated and purified by means of a silica gel column chromatography (eluted with ethyl acetate) to obtain 4-[3-(5-(4-chlorophenoxy)-2-pyridyl)-3-(3,4-dimethoxyphenyl)acryloxy]morpholine (Compound No.88) (300 mg) as a resinous solid.

From NMR data, it was found that this substance was a mixture of E-isomer and Z-isomer (about 1:3).

NMR (CDCl$_3$) δ ppm: 3.02 to 3.69 (8 H, m), 3.79 to 3.98 (6 H, m), 6.32 to 7.46 (10 H, m), 8.38 to 8.50 (1 H, m)

Typical examples of Compound [I] of the present invention, which can be produced in a manner similar to those of the above Examples 1 to 7 are shown in the following Table 3. The Table 3 includes the compounds obtained by the above Examples 1 to 7.

TABLE 3

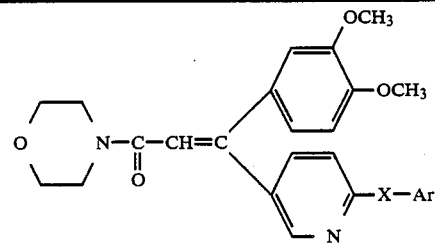

| Compound No. | Ar | X | Physical Data (NMR, δ ppm) olefin proton | aromatic proton |
|---|---|---|---|---|
| 1 | 2-Cl-phenyl | O | | (Cf. Ex. No. 1) |
| 2 | 3-Cl-phenyl | O | 6.33(1H, s; Z) | 6.77~7.43(8H, m), 7.63 (1H, d, d), 8.08(1H, d) |
| 3 | 4-Cl-phenyl | O | | (Cf. Ex. No. 2) |
| 4 | 2-F-phenyl | O | 6.20 and 6.30 (1H, s, s;E+Z) | 6.77~7.73(9H, m), 8.05 and 8.13(1H, d, d;E+Z) |

TABLE 3-continued
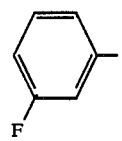
| Compound No. | Ar | X | Physical Data (NMR, δ ppm) olefin proton | aromatic proton |
|---|---|---|---|---|
| 5 | 3-F-C6H4- | O | 6.22 and 6.35 (1H, s, s;E+Z) | 6.80~7.10(7H, m), 7.23~7.73(2H, m), 8.12 and 8.22(1H, d, d;E+Z) |
| 6 | 4-F-C6H4- | O | 6.18 and 6.33 (1H, s, s;E+Z) | 6.80~7.27(8H, m), 7.50~7.73(1H, m), 8.07 and 8.17(1H, d, d;E+Z) |
| 7 | 2-Br-C6H4- | O | 6.20 and 6.32 (1H, s, s;E+Z) | 6.73~7.37(7H, m), 7.53~7.73(1H, m), 8.03 and 8.13(1H, d, d;E+Z) |
| 8 | 3-Br-C6H4- | O | 6.22 and 6.35 (1H, s, s;E+Z) | 6.67~7.70(9H, m), 8.12 and 8.22(1H, d, d; E+Z) |
| 9 | 4-Br-C6H4- | O | 6.17 and 6.30 (1H, s, s;E+Z) | 6.73~7.70(9H, m), 7.99~8.20(1H, m) |
| 10 | 4-I-C6H4- | O | 6.23 and 6.37 (1H, s, s;E+Z) | 6.75~7.83(9H, m), 8.03~8.30(1H, m) |
| 11 | 2,4-Cl2-C6H3- | O | 6.20 and 6.33 (1H, s, s;E+Z) | 6.83(3H, s), 6.84~7.74 (5H, m), 8.17(1H, m) |
| 12 | 3,4-Cl2-C6H3- | O | 6.37(1H, s, Z) | 6.80~7.73(8H, m), 8.07 (1H, d) |
| 13 | 2,5-Cl2-C6H3- | O | 6.20 and 6.33 (1H, s, s;E+Z) | 6.70~7.70(8H, m), 8.17 (1H, d) |

TABLE 3-continued
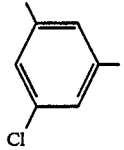
| Compound No. | Ar | X | Physical Data (NMR, δ ppm) olefin proton | aromatic proton |
|---|---|---|---|---|
| 14 | 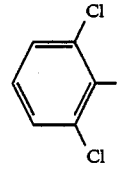 2,4-Cl,Cl | O | 6.23 and 6.38 (1H, s, s;E+Z) | 6.73~7.40(7H, m), 7.57~ 7.77(1H, m), 8.12 and 8.22(1H, d, d,E+Z) |
| 15 | 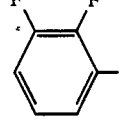 2,6-Cl,Cl | O | 6.21 and 6.30 (1H, s, s;E+Z) | 6.70~7.75(8H, m), 8.08 (1H, d, d;E+Z) |
| 16 | 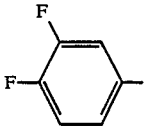 2,3-F,F | O | 6.20 and 6.33 (1H, s, s;E+Z) | 6.83(3H, s), 6.93~7.27 (4H, m), 7.57~7.73(1H, m), 8.07 and 8.15(1H, d, d;E+Z) |
| 17 | 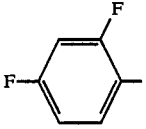 3,4-F,F | O | | |
| 18 | 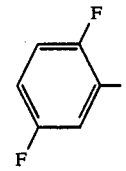 2,4-F,F | O | 6.20 and 6.32 (1H, s, s;E+Z) | 7.53~7.73(1H, m), 6.73~ 7.40(7H, m), 8.02 and 8.12(1H, d, d;E+Z) |
| 19 | 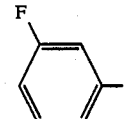 2,5-F,F | O | | |
| 20 | 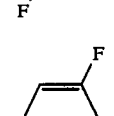 3,5-F,F | O | 6.23 and 6.37 (1H, s, s;E+Z) | 6.50~7.10(7H, m), 7.57~ 7.73(1H, m), 8.12 and 8.22(1H, d, d;E+Z) |
| 21 | 2,6-F,F | O | 6.20 and 6.30 (1H, s, s;E+Z) | 7.07~7.30(7H, m), 7.53~ 7.77(1H, m), 8.00~ 8.17(1H, m;E+Z) |

TABLE 3-continued
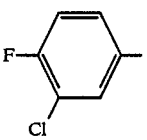
| Compound No. | Ar | X | Physical Data (NMR, δ ppm) olefin proton | aromatic proton |
|---|---|---|---|---|
| 22 | 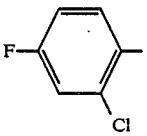 | O | 6.20 and 6.35 (1H, s, s;E+Z) | 6.73~7.73(7H, m), 7.53~ 7.73(1H, m), 8.83 and 8.18(1H, d, d;E+Z) |
| 23 | 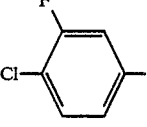 | O | 6.20 and 6.32 (1H, s, s;E+Z) | 6.73~7.37(7H, m), 7.53~ 7.73(1H, m), 8.03 and 8.13(1H, d, d;E+Z) |
| 24 | 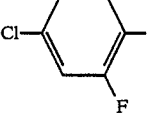 | O | 6.21 and 6.36 (1H, s, s;E+Z) | 6.70~7.20(7H, m), 7.60, 7.70(1H, d, d, :E+Z), 8.07, 8.18(1H, d, d;E+Z) |
| 25 | 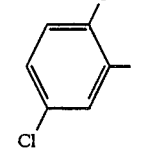 | O | 6.20 and 6.33 (1H, s, s;E+Z) | 6.80~7.33(7H, m), 7.53~ 7.73(1H, m), 8.03 and 8.13(1H, d, d;E+Z) |
| 26 | 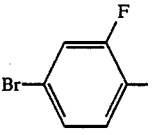 | O | | |
| 27 | 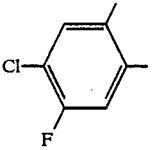 | O | 6.20 and 6.33 (1H, s, s;E+Z) | 6.77~7.47(7H, m), 7.53~ 7.73(1H, m), 8.03 and 8.13(1H, d, d;E+Z) |
| 28 | 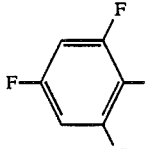 | O | | |
| 29 |  | O | | |

TABLE 3-continued

[Structure: morpholine-N-C(=O)-CH=C with 3,4-dimethoxyphenyl group and pyridyl-X-Ar group]

| Compound No. | Ar | X | olefin proton | aromatic proton |
|---|---|---|---|---|
| 30 | 2,3,5,6-tetrafluorophenyl | O | 6.10 and 6.23 (1H, s, s;E+Z) | 6.60~7.15(5H, m), 7.43~7.63(1H, m), 7.91(1H, d,d) |
| 31 | pentafluorophenyl | O | 6.22 and 6.37 (1H, s, s;E+Z) | 6.70~7.00(3H, m), 7.00~7.23(1H, m), 7.70(1H, dd), 8.00 and 8.08 (1H, d, d;E+Z) |
| 32 | 2-CH₃-phenyl | O | 6.18 and 6.30 (1H, s, s;E+Z) | 6.73~7.40(9H, m), 8.09 and 8.20(1H, d, d;E+Z) |
| 33 | 4-CH₃-phenyl | O | 6.17 and 6.30 (1H, s, s;E+Z) | 6.73~7.33(8H, m), 7.47~7.66(1H, m), 8.07 and 8.17(1H, d, d;E+Z) |
| 34 | 3-CH₃-phenyl | O | 6.18 and 6.30 (1H, s, s;E+Z) | 6.73~7.67(9H, m), 8.10 and 8.20(1H, d, d;E+Z) |
| 35 | 4-C₂H₅-phenyl | O | 6.17 and 6.29 (1H, s, s;E+Z) | 6.74~7.39(8H, m), 7.48~7.68(1H, m), 8.08 and 8.17(1H, d, d;E+Z) |
| 36 | 4-n-C₃H₇-phenyl | O | 6.18 and 6.30 (1H, s, s;E+Z) | 6.75~7.39(8H, m), 7.49~7.68(1H, m), 8.09 and 8.17(1H, d, d;E+Z) |
| 37 | 4-t-C₄H₉-phenyl | O | 6.16 and 6.30 (1H, s, s;E+Z) | 6.73~7.26(8H, m), 7.50~7.63(1H, m), 8.10 and 8.20(1H, s, s;E+Z) |
| 38 | 2,4-dimethylphenyl | O | 6.20 and 6.30 (1H, s, s;E+Z) | 6.83~8.66(8H, m), 8.10 and 8.23(1H, d, d;E+Z) |

TABLE 3-continued

[Structure: morpholine-N-C(=O)-CH=C with two substituents: one is 3,4-dimethoxyphenyl, the other is a pyridine bearing X-Ar]

| Compound No. | Ar | X | Physical Data (NMR, δ ppm) | |
|---|---|---|---|---|
| | | | olefin proton | aromatic proton |
| 39 | 4-Cl, 3-CH₃-phenyl | O | 6.20 and 6.33 (1H, s, s;E+Z) | 6.67~7.67(8H, m), 8.16 and 8.27(1H, d, d;E+Z) |
| 40 | 2-CH₃, 5-Cl-phenyl | O | 6.21 and 6.35 (1H, s, s;E+Z) | 6.68~7.70(8H, m), 8.16 and 8.29(1H, d, d;E+Z) |
| 41 | 3-CF₃-phenyl | O | 6.22 and 6.33 (1H, s, s;E+Z) | 6.73~7.73(9H, m), 8.07 and 8.17(1H, s, s;E+Z) |
| 42 | 4-CF₃-phenyl | O | 6.22 and 6.37 (1H, s, s;E+Z) | 6.67~7.07(3H, m), 7.13~7.77(5H, m), 8.08 and 8.19(1H, d, d;E+Z) |
| 43 | 3-CF₃, 2-Cl-phenyl | O | | |
| 44 | 2-F, 4-CH₃-phenyl (mislabeled) | O | | |
| 45 | 3-CH₃, 4-F-phenyl | O | | |
| 46 | 2-OCH₃-phenyl | O | 6.19 and 6.27 (1H, s, s;E+Z) | 6.70~7.37(8H, m), 7.49~7.68(1H, m), 8.02~8.22(1H, m) |
| 47 | 3-OCH₃-phenyl | O | 6.20 and 6.32 (1H, s, s;E+Z) | 6.68~6.99(7H, m), 7.19~7.70(2H, m), 8.09~8.29(1H, m) |

TABLE 3-continued

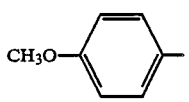

| Compound No. | Ar | X | Physical Data (NMR, δ ppm) olefin proton | aromatic proton |
|---|---|---|---|---|
| 48 | CH$_3$O—⟨⟩— | O | 6.17 and 6.30 (1H, s, s;E+Z) | 6.77~7.27(8H, m), 7.53 (1H, d), 7.63(1H, d), 8.0 7 and 8.17(1H, s, s;E+Z) |
| 49 | C$_2$H$_5$O—⟨⟩— | O | 6.17 and 6.30 (1H, s, s;E+Z) | 6.67~7.19(9H, m), 7.45~ 7.65(1H, m), 8.04~ 8.22(1H, m) |
| 50 | 2-Cl, 4-MeO-C$_6$H$_3$— | O | 6.21 and 6.33 (1H, s, s;E+Z) | 6.70~7.34(7H, m), 7.51~ 7.71(1H, m), 8.05~ 8.26(1H, m) |
| 51 | 3-F, 4-CH$_3$O-C$_6$H$_3$— | O | 6.21 and 6.35 (1H, s, s;E+Z) | 6.71~7.15(7H, m), 7.51~ 7.72(1H, m), 8.10 and 8.20(1H, d, d;E+Z) |
| 52 | CF$_2$HO—⟨⟩— | O | 6.21 and 6.34 (1H, s, s;E+Z) | 6.70~7.02(4H, m), 7.15~ 7.32(4H, m), 7.52~ 7.78(1H, m), 8.06~8.26 (1H, m) |
| 53 | CF$_2$H—CF$_2$O—⟨⟩— | O | | |
| 54 | CH$_3$S—⟨⟩— | O | 6.18 and 6.32 (1H, s, s;E+Z) | 6.83~7.90(9H, m), 8.08 and 8.18(1H, d, d;E+Z) |
| 55 | CF$_2$HS—⟨⟩— | O | | |
| 56 | CF$_2$H—CF$_2$S—⟨⟩— | O | | |
| 57 | 1-naphthyl | O | 6.20 and 6.30 (1H, s, s;E+Z) | 6.73~7.07(4H, m), 7.23~ 8.07(8H, m), 8.10 and 8.18(1H, d, d;E+Z) |

TABLE 3-continued

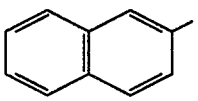

| Compound No. | Ar | X | Physical Data (NMR, δ ppm) olefin proton | aromatic proton |
|---|---|---|---|---|
| 58 | 2-naphthyl | O | 6.20 and 6.32 (1H, s, s;E+Z) | 6.80~8.00(12H, m), 8.10 and 8.20(1H, d, d;E+Z) |
| 59 | 4-Cl-phenyl | S | | (Cf. Ex. No. 3) |
| 60 | 2,3,5,6-tetrafluorophenyl | S | 6.23 and 6.36 (1H, s, s;E+Z) | 6.68~7.07(3H, m), 7.10~7.62(3H, m), 8.23~8.46(1H, m), |
| 61 | pentafluorophenyl | S | | |
| 62 | phenyl | —N(CH₃)— | | (Cf. Ex. No. 5) |
| 63 | phenyl | OCH₂ | | (Cf. Ex. No. 4) |
| 64 | 2-Cl-phenyl | OCH₂ | 6.18 and 6.28 (1H, s, s;E+Z) | 6.70~6.97(4H, m), 7.17~7.67(5H, m), 8.12 and 8.18(1H, d, d;E+Z) |
| 65 | 3-Cl-phenyl | OCH₂ | 6.19 and 6.29 (1H, s, s;E+Z) | 6.71~6.97(4H, m), 7.23~7.63(5H, m), 8.12 and 8.18(1H, d, d;E+Z) |
| 66 | 4-Cl-phenyl | OCH₂ | 6.19 and 6.29 (1H, s, s;E+Z) | 6.70~6.98(4H, m), 7.26~7.63(5H, m), 8.11 and 8.17(1H, d, d;E+Z) |

TABLE 3-continued

[Structure: morpholine-N-C(=O)-CH=C(Ar1)(pyridyl-X-Ar), where Ar1 = 3,4-dimethoxyphenyl]

| Compound No. | Ar | X | olefin proton | aromatic proton |
|---|---|---|---|---|
| 67 | 2-F-C6H4 | OCH2 | 6.18 and 6.28 (1H, s, s;E+Z) | 6.70~6.92(3H, m), 6.93~7.65(6H, m), 8.12 and 8.18(1H, d, d;E+Z) |
| 68 | 4-F-C6H4 | OCH2 | 6.17 and 6.28 (1H, s, s;E+Z) | 6.67~7.60(9H, m), 8.10 and 8.17(1H, d, d;E+Z) |
| 69 | 2-CH3-C6H4 | OCH2 | 6.19 and 6.28 (1H, s, s;E+Z) | 6.67~7.00(4H, m), 7.15~7.63(5H, m), 8.13 and 8.20(1H, d, d;E+Z) |
| 70 | 4-CH3-C6H4 | OCH2 | 6.17 and 6.27 (1H, s, s;E+Z) | 6.67~6.96(4H, m), 7.10~7.60(5H, m), 8.10 and 8.17(1H, d, d;E+Z) |
| 71 | 4-CH3O-C6H4 | OCH2 | 6.17 and 6.27 (1H, s, s;E+Z) | 6.69~7.03(5H, m), 7.25~7.55(4H, m), 8.11 and 8.18(1H, d, d;E+Z) |
| 72 | 2,6-F2-C6H3 | OCH2 | 6.19 and 6.29 (1H, s, s;E+Z) | 6.65~7.10(6H, m), 7.15~7.55(2H, m), 8.11, 8.18(1H, d, d;E+Z) |
| 73 | 2,4-F2-C6H3 | OCH2 | 6.18 and 6.29 (1H, s, s;E+Z) | 6.68~7.05(6H, m), 7.35~7.66(2H, m), 8.12 and 8.18(1H, d, d;E+Z) |
| 74 | 2,4-Cl2-C6H3 | OCH2 | 6.18 and 6.29 (1H, s, s;E+Z) | 6.68~7.00(4H, m), 7.17~7.64(4H, m), 8.11, 8.17(1H, d, d;E+Z) |
| 75 | 2-CH3-C6H4 | OCH2 | 6.19 and 6.29 (1H, s, s;E+Z) | 6.67~7.00(4H, m), 7.25~7.87(5H, m), 8.12 and 8.19(1H, d, d;E+Z) |

TABLE 3-continued

| Compound No. | Ar | X | Physical Data (NMR, δ ppm) olefin proton | aromatic proton |
|---|---|---|---|---|
| 76 |  | OCH$_2$ | 6.20 and 6.30 (1H, s, s;E+Z) | 6.69~7.61(4H, m), 8.14, 8.21(1H, d, d;E+Z) |
| 77 | 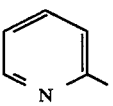 | OCH$_2$ | 6.19 and 6.29 (1H, s, s;E+Z) | 6.32~6.53(2H, m), 6.70~6.90(4H, m), 7.39~7.57(2H, m), 8.08, 8.15 (1H, d, d;E+Z) |
| 78 | 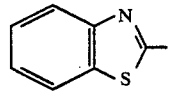 | OCH$_2$ | 6.18 and 6.28 (1H, s, s;E+Z) | 6.76~7.00(4H, m), 7.13~7.85(4H, m), 8.10, 8.17 (1H, d, d;E+Z), 8.63 (1H, d) |
| 79 |  | OCH$_2$ | 6.20 and 6.30 (1H, s, s;E+Z) | 6.77~7.10(4H, m), 7.25~7.67(3H, m), 7.83 8.25(3H, m) |
| 80 | 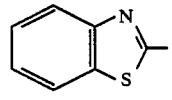 | O | 6.21 and 6.36 (1H, s, s;E+Z) | 6.80~7.09(4H, m), 7.27~7.76(3H, m), 8.07, 8.17(1H, d, d;E+Z), 8.40~8.70(2H, m) |
| 81 | 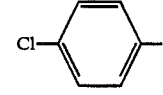 | S | 6.31 and 6.42 (1H, s, s;E+Z) | 6.70~7.00(3H, m), 7.33~7.70(5H, m), 7.75~8.15(3H, m), 8.50, 8.60 (1H, d, d;E+Z) |
| 82 |  | Bond | 6.37 and 6.47 (1H, s, s;E+Z) | 6.86~7.01(3H, m), 7.42~7.88(4H, m), 7.93~8.15(2H, m), 8.58~8.79(1H, m) |
| 83 |  | CH$_2$ | | |
| 84 |  | CH$_2$CH$_2$ | 6.23 and 6.35 (1H, s, s;E+Z) | 6.70~7.68(10H, m), 8.43~8.65(1H, m) |
| 85 | 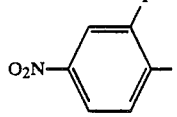 | O | 6.21 and 6.37 (1H, s, s;E+Z) | 6.77~6.95(3H, m), 6.98~7.80(3H, m), 7.98~8.25(3H, m) |
| 86 | 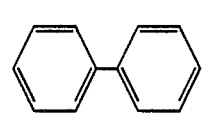 | O | 6.20 and 6.32 (1H, s, s;E+Z) | 6.72~7.04(4H, m), 7.16~7.76(10H, m), 8.08~8.30(1H, m) |

TABLE 3-continued
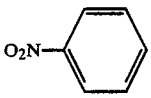
| Compound No. | Ar | X | olefin proton | aromatic proton |
|---|---|---|---|---|
| 87 | 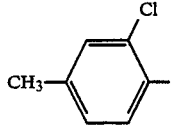 | O | | |
| 89 | 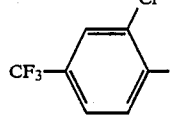 | O | 6.25 and 6.39 (1H, s, s;E+Z) | 6.70~7.60(8H, m), 8.16, 8.30(1H, d, d) |
| 90 | 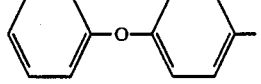 | O | 6.23 and 6.35 (1H, s, s;E+Z) | 6.75~7.8(8H, m), 8.10 (1H, d, d) |
| 91 | 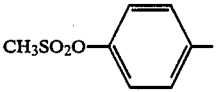 | O | 6.20 and 6.32 (1H, s, s;E+Z) | 6.79~7.72(14H, m), 8.07~8.25(1H, m) |
| 92 | 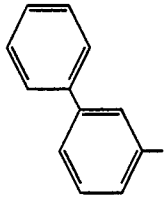 | O | 6.34(1H, s) | 6.80~7.40(8H, m), 7.64 (1H, d, d), 8.08(1H, d) |
| 93 | 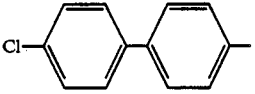 | O | 6.20 and 6.32 (1H, s, s;E+Z) | 6.71~7.06(5H, m), 7.07~7.73(9H, m), 8.05~8.32(1H, m) |
| 94 | 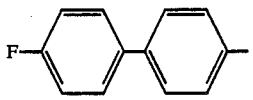 | O | 6.20 and 6.33 (1H, s, s;E+Z) | 6.70~7.08(3H, m), 7.18~7.73(10H, m), 8.12~8.46(1H, m) |
| 95 | 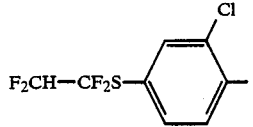 | O | | |
| 96 |  | O | 6.25 and 6.50 (1H, s, s;E+Z) | 6.90~7.70(7H, m), 8.30, 8.35(1H, d, d;E+Z) |

TABLE 3-continued

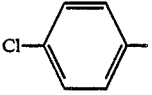

| Compound No. | Ar | X | Physical Data (NMR, δ ppm) olefin proton | aromatic proton |
|---|---|---|---|---|
| 97 | 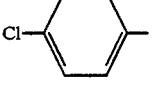 4-Cl-C6H4- | SCH2 | 6.22 and 6.32 (1H, s, s;E+Z) | 6.68~6.97(3H, m), 7.03~ 7.50(6H, m), 8.35, 8.43(1H, d, d;E+Z) |
| 98 | 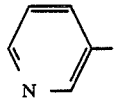 4-Cl-C6H4- | SO2CH2 | 6.36 and 6.59 (1H, s, s;E+Z) | 6.63~6.93(3H, m), 7.06~ 7.40(4H, m), 7.60~ 7.90(2H, m), 8.66, 8.75(1H, d, d;E+Z) |
| 99 | 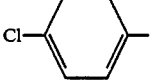 3-pyridyl | OCH2 | 6.18 and 6.29 (1H, s, s;E+Z) | 6.70~6.97(4H, m), 7.22~7.44 (1H, m), 7.48, 7.57(1H, d, d; E+Z), 7.83(1H, d), 8.12, 8.18 (1H, d, d;E+Z), 8.46~8.90 (2H, m) |
| 100 | 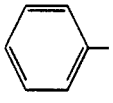 4-Cl-C6H4- | —N(CH3)— | 6.19 and 6.20 (1H, s, s;E+Z) | 6.81(2H, s), 7.26~8.19(8H, m) |
| 101 | 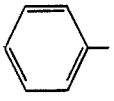 C6H5- | —C≡C— | 6.31 and 6.44 (1H, s, s;E+Z) | 6.71~6.99(3H, m), 7.26~ 7.73(7H, m), 8.53~ 8.73(1H, m) |
| 102 | 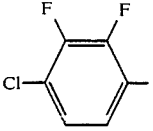 C6H5- | O | 6.20 and 6.30 (1H, s, s;E+Z) | 6.77~7.67(10H, m). 8.08 and 8.19(1H, d, d;E+Z) |
| 103 | 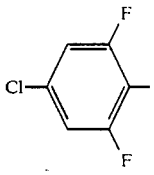 3-Cl-2,4-F2-C6H2- | O | 6.21 and 6.35 (1H, s, s;E+Z) | 6.75~7.73(6H, m), 7.66 and 7.76(1H, d, d:E+Z), 8.07, 8.13(1H, d, d, E+Z) |
| 104 | 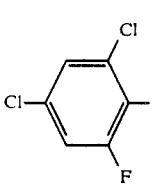 4-Cl-2,6-F2-C6H2- | O | 6.20 and 6.30 (1H, s, s;E+Z) | 6.60~7.10(6H, m), 7.50~7.77(1H, m, E+Z), 8.00~8.20(1H, m, E+Z) |
| 105 | 2,4-Cl2-6-F-C6H2- | O | 6.30 and 6.50 (1H, s, s;E+Z) | 6.67~6.80(5H, m), 7.30 (1H, m), 7.60(1H, dt), 8.30, 8.40(1H, d, d, E+Z) |

TABLE 3-continued

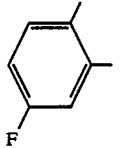

| Compound No. | Ar | X | Physical Data (NMR, δ ppm) olefin proton | aromatic proton |
|---|---|---|---|---|
| 106 | 2-Br-4-F-phenyl | O | 6.30 and 6.51 (1H, s, s;E+Z) | 6.67~6.82(6H, m), 7.30 (1H, m), 7.61(1H, dt), 8.32, 8.40(1H, d, d, E+Z) |
| 107 | 2-Cl-4-Br-5-F-phenyl | O | 6.21 and 6.32 (1H, s, s;E+Z) | 6.77~6.91(3H, m), 6.99~7.78(4H, m), 8.01, 8.09(1H, d, d, E+Z) |
| 108 | 2-F-4-Br-6-F-phenyl | O | 6.18 and 6.30 (1H, s, s;E+Z) | 6.70~7.33(6H, m), 7.57~7.73(1H, m), 8.01, 8.08(1H, d, d, E+Z) |
| 109 | 2-Cl-4-Br-phenyl | O | 6.27 and 6.30 (1H, s, s;E+Z) | 6.90~7.70(8H, m), 8.03, 8.10(1H, d, d:E+Z) |
| 110 | 2-CH₃-4-Br-phenyl | O | 6.20 and 6.32 (1H, s, s;E+Z) | 6.70~7.03(5H, m), 7.30~7.70(3H, m), 8.07, 8.19(1H, d, d, E+Z) |
| 111 | 2-CH₃-4-Br-phenyl | O | 6.20 and 6.33 (1H, s, s;E+Z) | 6.73~7.13(6H, m), 7.50~ 7.70(2H, m), 8.08, 8.18(1H, d, d, E+Z) |
| 112 | 2-MeO-4-Br-phenyl | O | 6.19 and 6.31 (1H, s, s;E+Z) | 6.70~7.00(6H, m), 7.20~ 7.73(2H, m), 8.10 and 8.20(1H, d, d, E+Z) |
| 113 | 4-Cl-phenyl | CH₂ | 6.24 and 6.38 (1H, s, s;E+Z) | 6.67~7.63(9H, m), 8.42~8.68(1H, m), |

FORMULATION EXAMPLE 1

Emulsifiable Concentrates

The emulsifiable concentrates were prepared by homogeneously mixing the compound No.1 (20 weight %), xylene (75 weight %) and polyoxyethylene alkylaryl ether (Nonipol 85®, manufactured by San-yo Chemical Industries Co., Ltd.) (5 weight %).

FORMULATION EXAMPLE 2

Wettable Powders

The wettable powders were prepared by mixing and crushing the compound No. 2 (50 weight %), diatomaceous earth (44 weight %) and polyoxyethylene alkylaryl ether (Nonipol 85®, manufactured by San-yo Chemical Industries Co., Ltd.) (6 weight %).

FORMULATION EXAMPLE 3

Dusts

The dusts were prepared by homogeneously mixing the compound No.3 (3 weight %), clay (40 weight %) and talc (57 weight %).

What is claimed is:

1. A compound of the formula:

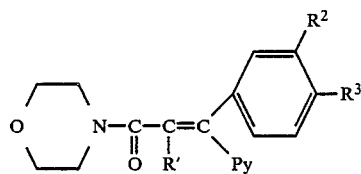

wherein $R^1$ is hydrogen or a lower alkyl group; $R^2$ and $R^3$ independently are a lower alkoxyl group; and Py is an optionally substituted pyridyl group with the substitutents being non heterocyclic groups, or a salt thereof.

2. A compound as claimed in claim 1, wherein Py is a the formula:

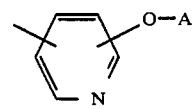

wherein A is an aryl group of 6 to 10 carbon atoms which is substituted by (1) a halogen, (2) an alkyl group of 1 to 3 carbon atoms, or/and (3) an alkoxy group of 1 to 3 carbon atoms, the number of the substituents being to 1 to 3.

3. A compound as claimed in claim 2, wherein the group of the formula Py is a group of the formula:

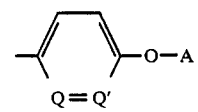

wherein either of Q and Q' is N, and the other is CH, and the other symbols are as defined above.

4. A compound as claimed in claim 1, wherein $R^1$ is hydrogen.

5. A compound as claimed in claim 1, wherein $R^2$ and $R^3$ independently are methoxy.

6. A compound as claimed in claim 1, namely 4-[3-(2-(4-chlorophenoxy)-5-pyridyl)-3-(3,4-dimethoxyphenyl)-acryloyl]morpholine.

7. A compound as claimed in claim 1, namely 4-[3-(2-(4-bromo-2-fluorophenoxy)-5-pyridyl)-3-(3,4-dimethoxyphenyl)acryloyl]morpholine.

8. A compound as claimed in claim 1, namely 4-[3-(2-(4-bromo-2-methylphenoxy)-5-pyridyl)-3-(3,4-dimethoxyphenyl)acryloyl]morpholine.

9. A fungicidal composition which comprises an effective fungicidal amount of a compound claimed in claim 1 and a carrier.

* * * * *